United States Patent
Yang et al.

(10) Patent No.: US 12,071,644 B2
(45) Date of Patent: Aug. 27, 2024

(54) XYLANASE VARIANTS AND METHODS

(71) Applicant: Fornia BioSolutions, Inc., Hayward, CA (US)

(72) Inventors: Jie Yang, Foster City, CA (US); William Buchanan Porterfield, Oakland, CA (US); Xiyun Zhang, San Ramon, CA (US); Goutami Banerjee, Daly City, CA (US); Khin Oo, Daly City, CA (US); Wenhua Lu, Dublin, CA (US)

(73) Assignee: Fornia Biosolutions, Inc., Hayward, CA (US)

( * ) Notice: Subject to any disclaimer, the term of this patent is extended or adjusted under 35 U.S.C. 154(b) by 0 days.

(21) Appl. No.: 17/552,423

(22) Filed: Dec. 16, 2021

(65) Prior Publication Data
US 2022/0195410 A1 Jun. 23, 2022

Related U.S. Application Data

(60) Provisional application No. 63/126,832, filed on Dec. 17, 2020.

(51) Int. Cl.
| | |
|---|---|
| C12N 9/24 | (2006.01) |
| A23K 20/189 | (2016.01) |
| A23K 50/30 | (2016.01) |
| A23K 50/75 | (2016.01) |
| C12N 15/63 | (2006.01) |

(52) U.S. Cl.
CPC ............. *C12N 9/248* (2013.01); *C12N 15/63* (2013.01); *A23K 20/189* (2016.05); *A23K 50/30* (2016.05); *A23K 50/75* (2016.05)

(58) Field of Classification Search
CPC ...... C12N 9/248; C12N 15/63; C12N 9/2477; A23K 20/189; A23K 50/30; A23K 50/75
See application file for complete search history.

(56) References Cited

FOREIGN PATENT DOCUMENTS

CN 108103047 A * 6/2018

OTHER PUBLICATIONS

Murad, H. A., and H. H. Azzaz. "Cellulase and dairy animal feeding." Biotechnology 9.3 (2010): 238-256 (Year: 2010).*
Machine Translation of CN-108103047-A, (Jun. 2018).*
M.J. Betts, R.B. Russell. "Isoleucine." Amino acid properties and consequences of substitutions. In Bioinformatics for Geneticists, M.R. Barnes, I.C. Gray eds, Wiley, 2003 (Year: 2003).*
M.J. Betts, R.B. Russell. "Lysine." Amino acid properties and consequences of substitutions. In Bioinformatics for Geneticists, M.R. Barnes, I.C. Gray eds, Wiley, 2003 (Year: 2003).*
Bajaj, Priyanka, and Ritu Mahajan. "Cellulase and xylanase synergism in industrial biotechnology." Applied microbiology and biotechnology 103 (2019): 8711-8724 (Year: 2019).*

* cited by examiner

*Primary Examiner* — Neil P Hammell
*Assistant Examiner* — Kyle T Rega
(74) *Attorney, Agent, or Firm* — Morgan, Lewis & Bockius LLP

(57) ABSTRACT

The present invention relates to variant xylanase enzymes and their use thereof.

28 Claims, 20 Drawing Sheets
Specification includes a Sequence Listing.

Figure 1A

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00118607 | + | + | + | - | S5I |
| CL00118618 | + | + | ++ | - | T51C |
| CL00118627 | ++ | ++ | ++ | + | K15T |
| CL00118636 | - | ++ | - | - | G25E |
| CL00118652 | + | + | + | - | S5K |
| CL00118703 | + | + | + | - | T51E |
| CL00118730 | ++ | ++ | ++ | - | K20C |
| CL00118746 | + | + | - | + | T51R |
| CL00118796 | ++ | + | ++ | - | Q1P |
| CL00118827 | + | ++ | ++ | + | T51Q |
| CL00118859 | ++ | ++ | ++ | + | S8C |
| CL00118998 | + | + | ++ | - | K20V |
| CL00119021 | + | + | + | - | Q12T |
| CL00119029 | + | ++ | ++ | + | G26C |
| CL00119056 | ++ | + | ++ | + | S8H |
| CL00119075 | + | + | ++ | + | K20S |
| CL00119099 | + | - | ++ | + | K15R |
| CL00119107 | + | - | + | - | Q12L |
| CL00119177 | + | + | - | - | S6K |
| CL00119218 | ++ | + | ++ | - | Q1H |
| CL00119221 | + | + | ++ | - | S8R |
| CL00119267 | ++ | + | ++ | - | K15H |

Figure 1B

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00119374 | + | - | + | - | S5R |
| CL00119477 | + | + | ++ | ++ | G26T |
| CL00119485 | + | + | ++ | + | G26N |
| CL00119502 | - | - | + | + | K15V |
| CL00119607 | + | + | ++ | + | S6T |
| CL00119608 | + | - | ++ | - | S6H |
| CL00119625 | + | ++ | + | + | G26R |
| CL00119693 | ++ | + | ++ | ++ | V27W |
| CL00119790 | - | - | + | + | T149R |
| CL00119969 | ++ | + | ++ | - | G224K |
| CL00119993 | - | - | + | - | D225Y |
| CL00120434 | + | + | + | - | N160Q |
| CL00120469 | - | - | + | + | T190P |
| CL00120515 | + | - | ++ | - | G224L |
| CL00120582 | + | + | ++ | - | G224M |
| CL00120711 | - | - | + | - | G224T |
| CL00120794 | + | - | + | - | Q168S |
| CL00120812 | + | + | ++ | - | N160K |
| CL00120851 | + | + | + | + | T190H |
| CL00120856 | - | - | + | - | N160R |
| CL00121638 | - | - | + | + | S105D |
| CL00121654 | - | + | ++ | - | G56R |

Figure 1C

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00121679 | - | - | ++ | + | S90I |
| CL00121690 | - | - | ++ | + | F120Y |
| CL00121722 | - | + | + | + | N54D |
| CL00121736 | ++ | ++ | ++ | - | S89C |
| CL00121739 | - | + | + | + | F120H |
| CL00121749 | - | + | ++ | + | G56T |
| CL00121751 | + | + | ++ | - | S90C |
| CL00121761 | - | + | ++ | + | S105H |
| CL00121763 | + | + | ++ | + | V99A |
| CL00121945 | + | + | ++ | ++ | G56H |
| CL00121946 | + | + | ++ | + | S89V |
| CL00121991 | - | + | + | + | S133L |
| CL00122023 | + | ++ | + | - | S90E |
| CL00122049 | + | + | + | - | V99G |
| CL00122106 | ++ | ++ | ++ | ++ | S133T |
| CL00122152 | - | - | - | - | S90A |
| CL00122170 | + | ++ | ++ | - | S90F |
| CL00122174 | + | + | - | - | S133K |
| CL00122235 | - | ++ | - | - | N54G |
| CL00122288 | + | + | + | + | S89A |
| CL00122337 | - | + | - | - | G93L |
| CL00122371 | + | + | + | - | F120D |

Figure 1D

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00122387 | + | -- | + | - | S89T |
| CL00122398 | -- | ++ | -- | -- | S105I |
| CL00122418 | + | + | -- | + | S105N |
| CL00122441 | ++ | + | + | -- | H131F (G2P) |
| CL00122451 | -- | + | -- | -- | P121G |
| CL00122510 | + | - | + | - | F120S |
| CL00122612 | + | -- | -- | -- | H131P |
| CL00122917 | + | - | + | -- | G56K/P119Q |
| CL00122919 | - | - | + | -- | G56K/F120Y/S133D |
| CL00122972 | - | - | + | - | G56K/S178T |
| CL00122980 | - | - | + | -- | T51S/S133D |
| CL00123125 | - | - | + | -- | V27I/G56K/N160K |
| CL00123198 | + | + | + | -- | P121R/S133D/N160K |
| CL00123323 | + | + | ++ | + | G18S/V27I/G56K/N160K/L194M |
| CL00123332 | + | + | ++ | + | G18S/N160K |
| CL00123370 | ++ | - | ++ | -- | G18S/G28D |
| CL00123399 | + | + | + | -- | G56K/P119Q/P121R/S133D/L194M |
| CL00123452 | + | + | ++ | + | G18S/G56K/F120Y |
| CL00123466 | + | + | + | + | V27I/N160K |
| CL00123482 | + | + | + | + | T51S/P119Q/S133D/N160K/S178T |
| CL00123487 | + | + | - | + | G18S/T23S/G56K/P119Q/F120Y/P121R/S133D |
| CL00123521 | - | - | + | - | T51S/F120Y |
| CL00123534 | + | + | + | -- | G56K/S133D/N160K |
| CL00123565 | + | + | ++ | -- | T51S/G56K/F120Y/S178T |

Figure 1E

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00123674 | + | - | + | + | G56K/N160K |
| CL00123794 | + | + | + | - | T51S/G56K/S133D/N160K |
| CL00123961 | + | + | + | + | T51S/P119Q/F120Y/N160K |
| CL00128238 | - | - |  | -- | Q1P/S8R/K20V/T51C/S89C/S90H |
| CL00128245 | + | - |  | -- | Q1P/S8H/K20V |
| CL00128324 | + | + |  | -- | Q1P/K15T/K20C/V27W/V99A |
| CL00128325 | + | + |  | - | S8C/K20V/V27W/H131F |
| CL00128371 | ++ | ++ |  | + | S8H/H131F |
| CL00128404 | ++ | ++ |  | + | V27W/H131F (G3P) |
| CL00128414 | + | + |  | -- | Q1P/K20C/V27W |
| CL00128425 | + | + |  | - | K15T/K20V/V27W |
| CL00128434 | + | + |  | -- | K20C/V27W/S89V/S90H |
| CL00128450 | ++ | + |  | + | Q1P/S8H/K15T/V27W/H131F |
| CL00128466 | ++ | + |  | - | Q1P/S8C/K15T/K20V/V27W/S89T/H131F |
| CL00128468 | + | - |  | - | Q1P/S8H/K15H/V27W/H131F |
| CL00128470 | + | + |  | - | Q1P/S8H/V27W/S89T |
| CL00128483 | + | + |  | - | Q1P/S8R/S89A/S90H/H131F |
| CL00128485 | + | - |  | -- | K20V/V27W/T51C/S89C/S90H/H131F |
| CL00128507 | ++ | + |  | + | Q1P/H131F |
| CL00128513 | + | + |  | + | K15H/K20V/V27W/H131F/G224K |
| CL00128526 | + | + |  | -- | Q1P/S8R/K15T/K20V/V27W/S89A/S90H/V99A/H131F/G224L |

Figure 1F

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00128532 | + | + | | - | Q1P/S8H/T51C/H131F |
| CL00128534 | + | - | | - | Q1P/K20V/V27W/V99A/H131F |
| CL00128541 | + | - | | - - | Q1P/S8R/K20V/V27W/T51C/G224L |
| CL00128542 | ++ | + | | - | Q1P/S8R/K15T/K20C/V27W/S89A/H131F |
| CL00128550 | ++ | + | | | K15T/K20V/V27W/H131F |
| CL00128563 | + | - | | - | Q1P/S8R/K20C/V27W |
| CL00128574 | + | + | | + | S8H/K20V/V27W |
| CL00128576 | + | - | | - - | Q1P/S8H/K15H/K20V/V27W/S89C/S90H/V99A/H131F |
| CL00128598 | + | - | | + | Q1P/S8R/K15H/V27W/V99A |
| CL00128651 | + | + | | - | K15H/V27W |
| CL00128653 | + | + | | - | S90E/H131F |
| CL00128662 | + | - | | - - | Q1P/K15H/K20V/V27W/T51C/S90H/H131F |
| CL00128672 | ++ | + | | + | K15T/K20C/V27W/H131F |
| CL00128674 | + | + | | ++ | V27W/G224L |
| CL00128721 | + | + | | + | K20V/V27W/H131F |
| CL00128742 | + | - | | - | K15T/K20V/V27W/T51C/G224L |
| CL00128750 | + | - | | + | Q1P/S8C/H131F |
| CL00128792 | + | + | | - | Q1P/S8R/K15H/K20V/V27W/T51C/S90E |
| CL00128793 | + | + | | - | Q1P/S8R/V27W |
| CL00128830 | + | - | | - | Q1P/S8C/V27W/T51C/H131F |
| CL00128895 | + | + | | - | Q1P/S8H |
| CL00128909 | + | - | | - | K15T/K20C/V27W/S90H/H131F |

Figure 1G

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00128946 | + | - | | - | K15T/V27W/S90H |
| CL00128949 | ++ | - | | ++ | Q1P/K20V/H131F |
| CL00128971 | + | + | | ++ | K15T/V27W |
| CL00128975 | + | -- | | + | Q1P/H131F/G224L |
| CL00128980 | - | - | | - | S8C/K15T/K20V/V27W/T51C/S90H |
| CL00129016 | ++ | -- | | - | Q1P/K15T/K20C/V27W/T51C/S89C/S90H/H131F |
| CL00129028 | + | - | | + | Q1P/S8H/K20C/V27W |
| CL00129058 | + | ++ | | | Q1P/S90H/N160K/T190H |
| CL00129068 | ++ | ++ | | | Q1P/S5K/G26N/V27W/F120Y/Q168S/T190H |
| CL00129070 | ++ | ++ | | | Q12T/K20C/G26T/S89C/H131F/Q168S |
| CL00129072 | ++ | ++ | | | S51/K20S/S89T/V99A/F120D/H131F/Q168S/T190H |
| CL00129074 | ++ | ++ | | | Q1P/S5K/K20S/S89C/F120Y |
| CL00129089 | ++ | ++ | | | S6H/G56K/V99A/Q168S/T190H |
| CL00129101 | ++ | + | | | S8R/K20V/T190H |
| CL00129105 | ++ | ++ | | | K15T/G26T/G56K/H131F/N160K/T190H |
| CL00129123 | ++ | ++ | | | S8H/K20C/S105N/H131F/N160Q/Q168S |
| CL00129127 | + | + | | | Q1H/S5R/K15V/G56K/Q168S |
| CL00129135 | + | + | | | K20S/G56K/F120Y/N160Q/T190H |
| CL00129147 | ++ | ++ | | | S8R/H131F/T190H |
| CL00129149 | ++ | ++ | | | G26N/V27W/G56K/S90H/H131F/Q168S/T190H |
| CL00129159 | ++ | + | | | S89V/H131F/Q168S |
| CL00129170 | ++ | ++ | | | S5R/Q12L/K15T/G26N/V27W/G56K/F120Y/H131F |

Figure 1H

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00129184 | ++ | ++ | | | S6H/S8R/K20S/S89A/V99A |
| CL00129188 | ++ | ++ | | | Q1P/S5R/G26T/S90C/H131F/Q168S/T190H |
| CL00129205 | ++ | ++ | | | S8H/K20C/T51R/S89A/P121R/N160K/T190H |
| CL00129214 | ++ | ++ | | | Q1P/S5R/Q12T/K15V/G26T/V27W/S90E/H131F/G224K |
| CL00129223 | ++ | ++ | | | Q1P/S5R/K20S/G56K/S89C/H131F/N160K/Q168S/T190H |
| CL00129235 | - | + | | | Q1H/S5K/Q12L/S90H/S105N/T190H |
| CL00129243 | ++ | ++ | | | S8C/K20C/T51C/S89A/Q168S |
| CL00129259 | ++ | ++ | | | G26N/V27W/S105N/Q168S/G224L |
| CL00129263 | ++ | + | | | S5I/S90H/S105N/F120Y/P121R/H131F/Q168S/G224K |
| CL00129270 | ++ | ++ | | | S6H/S8C/K20S/T51S/F120Y/P121R/T190H |
| CL00129292 | - | + | | | S5K/V99G/T190H |
| CL00129332 | ++ | ++ | | | S5K/K20V/G56K/H131F/Q168S |
| CL00129374 | ++ | ++ | | | S8R/T51R/S89T/H131F/T190H |
| CL00129384 | ++ | ++ | | | Q1P/S5R/S8R/V99A/N160Q |
| CL00129394 | ++ | ++ | | | S8R/T51C/F120D/Q168S/G224L |
| CL00129396 | ++ | ++ | | | Q1P/V27W |
| CL00129400 | ++ | ++ | | | Q1P/Q12T/K20V/G56K/S105N/N160Q/T190H/G224K |
| CL00129401 | ++ | - | | | Q1H/S5I/Q12L/K15R/H131F |
| CL00129410 | ++ | ++ | | | S89C/F120D/H131F/N160Q/G224L |
| CL00129412 | ++ | ++ | | | K20C/P121R |
| CL00129444 | ++ | ++ | | | K20S/V27W/T51Q/S105N/F120D/P121R/N160Q/T190H/G224M |
| CL00129451 | ++ | ++ | | | Q1H/S8C/K20V/G56K/S89A/H131F/T190H/G224L |

Figure 1I

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00129458 | ++ | ++ | | | S8H/G26T |
| CL00129503 | ++ | ++ | | | S6H/S8C/K20S/S89C/T190H |
| CL00129516 | ++ | ++ | | | K20S/T51C/S89V/T190H |
| CL00129536 | ++ | ++ | | | Q1H/Q12L/K15R/V27W/G56K/V99A/N160K/T190H |
| CL00129564 | ++ | ++ | | | S8C/K15R/S105N/H131F/T190H |
| CL00129599 | ++ | ++ | | | Q1H/S5R/Q12L/K20C/G56K/H131F/T190H |
| CL00129606 | + | + | | | Q1H/S5I/Q12T/K15V/G26T/G56K/S90E/S105N/Q168S |
| CL00129622 | ++ | ++ | | | S6H/K20C/S89T |
| CL00129623 | ++ | ++ | | | Q1H/S5R/K15R/G26N/G56K/H131F/T190H/G224K |
| CL00129649 | ++ | + | | | S89V/V99G/T190H |
| CL00129687 | + | + | | | Q1H/S5I/Q12L/K15T/Q168S |
| CL00129698 | + | + | | | Q12L/K15R/S90H/H131F/Q168S/T190H |
| CL00129700 | + | + | | | Q1H/S5I/T190H |
| CL00129706 | ++ | ++ | | | Q1P/S8H/K20V/T51Q/S89T/V99A/F120D/T190H |
| CL00129709 | ++ | ++ | | | S8R/K20S/G56K/K86T/S89A/V99A/H131F |
| CL00129710 | ++ | + | | | S8C/Q12T/K15V/G56K/T190H |
| CL00129714 | ++ | ++ | | | K20S/S89C/F120Y/H131F/T190H |
| CL00129729 | ++ | ++ | | | Q1P/K20V/G56K/S90E/S105N/H131F |
| CL00129753 | ++ | ++ | | | S5I/K20S/G26N/V27W/G56K/S90H/S105N/Q168A/T190H |
| CL00129755 | ++ | ++ | | | Q1P/S2K/S6H/S8R/S105N/Q168S/G224K |
| CL00129768 | ++ | ++ | | | S8H/K20C/T51R/S89A/N160K/Q168S |
| CL00129774 | - | + | | | Q1H/S5R/Q12T/K15R/G26N/S89A/V99G/F120D/P121R/T190H/G224M |

Figure 1J

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00129783 | + | - | | | S8C/K20S/G56K/S89C/V99G/F120D/P121R/T190H |
| CL00129807 | ++ | ++ | | | S6H/S8H/K20C/T51R/S89A/P121R/T190H |
| CL00129824 | + | + | | | Q1P/S5K/T51Q/V99G |
| CL00129826 | ++ | ++ | | | Q1P/S5I/S89V/S105N/H131F/Q168S |
| CL00129831 | ++ | ++ | | | S8H/K15V/K20C/T51Q/S89A/S105N/Q168S |
| CL00129842 | ++ | ++ | | | Q1P/S5I/K15R/G26T/S89C/V99G/F120Y/N160Q/T190H/G224K |
| CL00129846 | ++ | ++ | | | S89C/H131F/Q168S/T190H |
| CL00129864 | ++ | ++ | | | Q1P/S5K/Q12L/K20C/T51Q/S89V/F120Y/N160K/Q168S/T190H |
| CL00129868 | ++ | + | | | Q1H/S5K/G56K/F120D/P121R/Q168S |
| CL00129877 | + | ++ | | | T51E/V99A/P121R/H131F/N160Q/Q168S/T190H/G224K |
| CL00129879 | ++ | ++ | | | Q1P/S5R/Q12T/K15H/G26N/V27W/G56K/S90C/S105N/T190H |
| CL00129884 | ++ | ++ | | | S6H/S8R/K20C/T51C/F120D/T190H |
| CL00129895 | ++ | + | | | S8R/K20S/F120D/P121R |
| CL00129897 | - | ++ | | | S5R/S105N/Q168S/T190H |
| CL00129914 | ++ | ++ | | | Q1H/S5R/K15V/G26N/V27W/H131F/Q168S/T190H |
| CL00129928 | + | + | | | Q1H/S5R/Q12L/K15T/S90E/S105N/H131F/Q168S |
| CL00129946 | ++ | ++ | | | K20V/S89V/V99A/N160K/Q168S/G224K |
| CL00129948 | ++ | ++ | | | S90C/S105N/H131F |
| CL00129956 | ++ | ++ | | | S6H/S8H/K20V/T190H |
| CL00129958 | - | + | | | S8H/T51E/V99G/Q168S/T190H |
| CL00129959 | + | ++ | | | S5R/Q12L/K20V/S89C/Q168S/T190H |
| CL00129969 | ++ | ++ | | | Q1P/S5K/Q12T/K15H/G26N/V27W/G56K/S89C/H131F |

Figure 1K

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00129979 | + | + | | | K15R/G56K/T190H |
| CL00130030 | ++ | ++ | | | Q1H/S5K/Q12T/K15T/G26T/G56K/S89C/H131F/N160K/Q168S |
| CL00130034 | + | + | | | S6H/S8R/K20V/T51E/S90H/S105N/H131F/T135S/Q168S/T190H |
| CL00130036 | ++ | ++ | | | Q1P/S5K/Q12L/K15R/G56K/S89T/F120D |
| CL00130043 | ++ | + | | | Q12L/H131F/N160K/T190H |
| CL00130053 | ++ | ++ | | | Q1H/S5R/Q12T/K15H/G26N/V27W/G56K/H131F |
| CL00130079 | ++ | ++ | | | Q1P/S5K/Q12T/G56K/S105N/H131F/Q168S/T190H/G224L |
| CL00130085 | - | + | | | V27W/S90C/V99G/S105N/F120Y/N160K/Q168S |
| CL00130134 | ++ | + | | | G56K/S90C/H131F/Q168S/T190H |
| CL00130147 | ++ | ++ | | | Q1P/S5R/G26T/G56K/S105N/H131F/Q168S/T190H |
| CL00130164 | ++ | + | | | S8C/T51E/S89A/V99A/H131F/Q168S/T190H |
| CL00130167 | ++ | ++ | | | S5K/K15H/G26T/S90H/H131F |
| CL00130170 | ++ | ++ | | | G26N/G56K/S89T/H131F/Q168S/T190H/G224K |
| CL00130234 | ++ | ++ | | | Q1P/Q12L/K15T/G26N/V27W/S90H/S105N/H131F/T190H |
| CL00130239 | + | - | | | G56K/S90C |
| CL00130240 | + | + | | | K20S/S89V/V99G/S105N/T190H |
| CL00130245 | + | - | | | S5I/G26N/G56K/V99G/S105N |
| CL00130284 | ++ | ++ | | | Q1P/S5R/G56K/H131F/N160K/T190H |
| CL00130306 | ++ | ++ | | | Q1H/S5I/K20V/S89C |
| CL00130315 | ++ | + | | | K20C/T51Q/S89C/V99G/F120D/P121R/T190H |
| CL00130328 | ++ | ++ | | | S8R/Q12T/K15V/T51E/S89A/V99A/F120D/P121R/T190H |
| CL00130336 | ++ | ++ | | | G26N/V27W/S105N/H131F/Q168S |

Figure 1L

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00130353 | + | ++ | | | S6H/S89T/V99A/F120D/P121R/N160Q/Q168S/T190H |
| CL00130356 | ++ | + | | | T51Q/H131F |
| CL00130373 | + | ++ | | | Q1P/S5R/Q12L/K15V/V27W/G56K/V99A/S105N/F120D/N160Q/Q168S |
| CL00130374 | ++ | ++ | | | Q1P/S5R/G26N/G56K/S90H/S105N/F120D/P121R/T190H |
| CL00130379 | ++ | + | | | S5R/Q12T/K20V/G56K/F120Y |
| CL00130398 | + | + | | | S105N/F120D/P121R/T190H |
| CL00130410 | ++ | ++ | | | S8R/K20C/G26N/V27W/G56K/H131F/T190H |
| CL00130436 | + | ++ | | | Q1H/V27W/G56K/S90C |
| CL00130438 | + | - | | | G56K/S90C/H131F/Q168S/T190H |
| CL00130442 | ++ | ++ | | | Q12L/K15R/V27W/G56K/S90E |
| CL00130475 | + | ++ | | | Q1H/S105N/T190H |
| CL00130478 | ++ | ++ | | | G56K/S89T/S105N/P121R/H131F/Q168S/G224K |
| CL00130482 | + | ++ | | | K20S/S89A/V99G/S105N/N160Q/T190H |
| CL00130496 | ++ | ++ | | | Q1P/P121R/H131F/N160Q/T190H |
| CL00130502 | ++ | ++ | | | K15V/T51Q/S89V/H131F/G224K |
| CL00130509 | ++ | ++ | | | Q1P/K20S/N160K/T190H |
| CL00130539 | ++ | ++ | | | S8H/G56K/S89V/F120Y/P121R/N160Q/Q168S/T190H |
| CL00130586 | ++ | ++ | | | Q1H/S5K/V27W/G56K/Q168S/T190H |
| CL00130590 | + | - | | | F120D/P121R/Q168S |
| CL00130593 | ++ | ++ | | | S8H/K20V/T51S/V99A/T190H |
| CL00130599 | ++ | ++ | | | S8R/T51E/S89T/V99G/N160K/T190H |
| CL00130604 | ++ | ++ | | | K20S/S89C/T190H |

Figure 1M

| Colony Tracking Number | Low pH performance w.r.t. G1P | pH 5.5 performance w.r.t. G1P | Low pH stability w.r.t. G1P | 90 °C thermo-stability w.r.t. G1P | Active Mutations w.r.t. G1P |
|---|---|---|---|---|---|
| CL00130618 | ++ | ++ | | | K20S/S90E/G224M |
| CL00130647 | ++ | ++ | | | K15V/G56K/S89T/T190H |
| CL00130653 | + | + | | | S6H/S8R/Q12L/K15V/G26T/V27W/G56K/Q168S |
| CL00130658 | ++ | ++ | | | Q1P/S5I/K20S/G56K/S90E/H131F/Q168S |
| CL00130664 | ++ | + | | | S6H/F120Y/T190H |
| CL00130673 | ++ | ++ | | | S8H/K20V/T51S |
| CL00130678 | ++ | + | | | S105N/H131F |
| CL00130685 | ++ | ++ | | | S5I/Q12T/K15H/G26T/V27W/G56K/S90H/S105N/H131F/N160K/T190H |
| CL00130688 | ++ | ++ | | | Q1H/S5R/G26T/G56K/S105N/H131F/G224K |
| CL00130703 | ++ | ++ | | | S5I/S89C/S105N/H131F/Q168S |
| CL00130715 | ++ | ++ | | | Q1P/S5R/Q12L/K15R/G56K/S90H/F120D/P121R/H131F/N160K |
| CL00130717 | ++ | + | | | S105N/H131F/Q168S |
| CL00130720 | ++ | ++ | | | S6H/S8R/K20V/G56K/F120D/P121R/H131F/T190H |
| CL00130731 | ++ | ++ | | | Q1P/S5I/G26N/V27W/S90E/H131F/Q168S/G224M |
| CL00130734 | + | + | | | G56K/T190H |
| CL00130740 | ++ | ++ | | | S8R/K20C/T51E/S89V/Q168S/G224M |
| CL00130756 | ++ | ++ | | | S8C/K20S/S89A/F120Y/P121R/N160Q |
| CL00130765 | + | + | | | S5R/S89T/F120Y/P121R/T190H |
| CL00130775 | ++ | ++ | | | G26N/V27W/G56K/S105N/H131F/Q168S |
| CL00130786 | ++ | ++ | | | S6H/S8R/S89A/F120Y |
| CL00130788 | + | ++ | | | Q1P/S5R/Q12L/K15R/G26T/S90H/Q168S/T190H |
| CL00131244 | ++ | ++ | ++ | – | K20C/H131F |
| CL00131369 | ++ | + | ++ | – | K20C/V27W/H131F |
| CL00135697 | ++ | + | – | – | G26T/V27W/H131F |

Figure 1N

| Colony Tracking Number | Low pH performance w.r.t. G1P | pH 5.5 performance w.r.t. G1P | Low pH stability w.r.t. G1P | 90 °C thermostability w.r.t. G1P | Active Mutations w.r.t. G1P |
|---|---|---|---|---|---|
| CL00135698 | ++ | + | + | + | V27W/S89A/H131F |
| CL00135699 | ++ | ++ | + | + | V27W/H131F/S133T |
| CL00135700 | ++ | ++ | + | + | G26T/V27W/S89A/H131F |
| CL00135701 | ++ | ++ | + | + | G26T/V27W/H131F/S133T |
| CL00135702 | ++ | ++ | ++ | + | V27W/S89A/H131F/S133T |
| CL00135703 | ++ | ++ | ++ | + | G26T/V27W/S89A/H131F/S133T |
| CL00135704 | + | ++ | + | + | G26T/V27W/S35R/S89A/H131F/S133R |
| CL00135705 | + | + | + | -- | V27W/N38Y/F52W/G56Y/H131F/G201L |

Figure 2

| Colony Tracking Number | Low pH performance w.r.t. G2P | pH 5.5 performance w.r.t. G2P | 90 °C thermo-stability w.r.t. G2P | Active Mutations w.r.t. G1P |
|---|---|---|---|---|
| CL00131089 | ++ | ++ | -- | K15H/K20C/H131F |
| CL00130872 | ++ | ++ | - | K15H/K20V/V27W/S89A/H131F |
| CL00131142 | ++ | ++ | -- | K15H/S89C/H131F |
| CL00130904 | ++ | ++ | - | K15H/V27W/H131F |
| CL00131169 | ++ | ++ | - | K15R/K20C/H131F |
| CL00131019 | ++ | ++ | -- | K15R/K20C/S89A/H131F |
| CL00130942 | ++ | ++ | -- | K15R/K20C/S89C/H131F |
| CL00130901 | ++ | ++ | - | K15R/K20C/S89V/H131F |
| CL00130860 | + | + | - | K15R/K20V/H131F |
| CL00130902 | + | + | - | K15R/S89A/H131F |
| CL00130871 | ++ | + | -- | K15R/S89C/H131F |
| CL00130844 | + | + | + | K15R/S89V/H131F |
| CL00131244 | ++ | + | -- | K20C/H131F |
| CL00131105 | ++ | ++ | -- | K20C/S89T/H131F |
| CL00130835 | + | + | -- | K20C/V27W/S89T/H131F/E185K |
| CL00131220 | + | + | + | K20V/H131F |
| CL00131084 | ++ | ++ | -- | K20V/S89C/H131F |
| CL00130899 | + | + | - | K20V/S89T/H131F |
| CL00131065 | ++ | ++ | - | K20V/S89V/H131F |
| CL00130925 | + | - | - | S89A/H131F |
| CL00131097 | ++ | ++ | -- | S89C/H131F |
| CL00131071 | ++ | ++ | -- | S8C/K15H/K20C/S89T/H131F |
| CL00130892 | + | + | -- | S8C/K20C/H131F |
| CL00130933 | + | ++ | -- | S8C/K20V/S89C/H131F |
| CL00131199 | ++ | + | -- | S8C/K20V/S89T/H131F |
| CL00130857 | ++ | ++ | -- | S8H/K15R/K20C/S89T/H131F |
| CL00130909 | ++ | ++ | -- | S8H/K20C/S89T/H131F |
| CL00130854 | ++ | ++ | -- | S8H/K20C/V27W/H131F |
| CL00130868 | ++ | ++ | - | S8H/K20V/H131F |
| CL00131051 | ++ | ++ | -- | S8H/K20V/S89C/H131F |
| CL00130847 | ++ | ++ | - | S8H/K20V/V27W/S89T/H131F |
| CL00131239 | ++ | ++ | -- | S8R/K15H/K20V/S89C/H131F |
| CL00130840 | ++ | ++ | -- | S8R/K15R/K20C/H131F |
| CL00130930 | ++ | ++ | -- | S8R/K20C/S89C/H131F |
| CL00130905 | ++ | + | - | V27W/S89C/H131F |
| CL00131126 | ++ | ++ | + | V27W/S89T/H131F |

Figure 3A

| Position | Residue in Xylanase G1P | Particular variants |
|---|---|---|
| 1 | Q | H, P |
| 2 | S | K |
| 5 | S | I, K, R |
| 6 | S | H, K, T |
| 8 | S | C, H, R |
| 12 | Q | L, T |
| 15 | K | H, R, T, V |
| 18 | G | S |
| 20 | K | C, S, V |
| 23 | T | S |
| 25 | G | E |
| 26 | G | C, N, R, T |
| 27 | V | I, W |
| 28 | G | D |
| 35 | S | R |
| 38 | N | Y |
| 51 | T | C, E, Q, R, S |
| 52 | F | W |
| 54 | N | D, G |
| 56 | G | H, K, R, T, Y |
| 86 | K | T |
| 89 | S | A, C, T, V |
| 90 | S | A, C, E, F, I, H |
| 93 | G | L |
| 99 | V | A, G |
| 105 | S | D, H, I, N |
| 119 | P | Q |
| 120 | F | D, H, S, Y |
| 121 | P | G, R |
| 131 | H | F, P |
| 133 | S | D, K, L, T, R |
| 135 | T | S |
| 149 | T | R |
| 160 | N | K, Q, R |
| 168 | Q | S, A |
| 178 | S | T |
| 185 | E | K |
| 190 | T | H, P |

Figure 3B

| Position | Residue in Xylanase G1P | Particular variants |
|---|---|---|
| 194 | L | M |
| 201 | G | L |
| 224 | G | K, L, M, T |
| 225 | D | Y |

Figure 4A

Xylanase G1P (wild-type) protein SEQ ID NO:1

QSFCSSASHSGQSVKVTGNKVGTIGGVGYELWADSGNNSATFYSDGSFSCTFQNAGDYLCRSGLSFDS
TKTPSQIGRMKADFKLVKQNSSNVGYSYVGVYGWTRSPLVEYYIVDNWLSPFPPGDWVGNKKHGSFT
IDGAQYTVYENTRTGPSIDGDTTFNQYFSIRQQARDCGTIDISAHFDQWEKLGMTMGKLHEAKVLGEA
GNVNGGASGTADFPYAKVYIGD

N.A. encoding Xylanase G1P (wild-type) protein SEQ ID NO:2

CAAAGTTTCTGTAGTTCAGCTTCTCACTCTGGACAAAGTGTAAAGGTAACCGGCAACAAGGTTGG
AACTATTGGTGGTGTTGGTTACGAATTATGGGCTGATAGTGGTAATAACAGTGCTACTTTCTATTC
TGATGGTTCCTTCTCATGTACTTTCCAAAATGCTGGGGATTACTTATGTCGTAGTGGTCTTTCTTTC
GATAGTACTAAGACCCCATCTCAAATTGGTCGTATGAAGGCTGATTTCAAACTTGTCAAACAAAAT
AGTTCCAATGTTGGTTATTCCTATGTTGGTGTTTACGGTTGGACTAGAAGTCCACTTGTCGAATACT
ACATTGTCGATAATTGGCTTAGTCCATTCCCACCAGGTGATTGGGTTGGTAACAAGAAGCATGGTT
CTTTCACTATTGATGGTGCTCAATACACTGTTTATGAAAACACTCGTACTGGTCCATCTATTGATGG
TGATACCACCTTCAATCAATACTTTAGTATTCGTCAACAAGCTCGTGATTGTGGTACCATTGATATT
TCTGCTCACTTTGATCAATGGGAAAAGCTTGGTATGACTATGGGTAAATTACATGAAGCCAAGGTT
TTAGGTGAAGCCGGTAACGTTAACGGTGGTGCCAGTGGTACCGCTGATTTCCCATACGCAAAGGTT
TACATTGGTGATTAG

Figure 4B

Xylanase G2P protein SEQ ID NO:3

QSFCSSASHSGQSVKVTGNKVGTIGGVGYELWADSGNNSATFYSDGSFSCTFQNAGDYLCRSGLSFDS
TKTPSQIGRMKADFKLVKQNSSNVGYSYVGVYGWTRSPLVEYYIVDNWLSPFPPGDWVGNKKFGSFT
IDGAQYTVYENTRTGPSIDGDTTFNQYFSIRQQARDCGTIDISAHFDQWEKLGMTMGKLHEAKVLGEA
GNVNGGASGTADFPYAKVYIGD

N.A. encoding Xylanase G2P protein SEQ ID NO:4

CAAAGTTTCTGTAGTTCAGCTTCTCACTCTGGACAAAGTGTAAAGGTAACCGGCAACAAGGTTGG
AACTATTGGTGGTGTTGGTTACGAATTATGGGCTGATAGTGGTAATAACAGTGCTACTTTCTATTC
TGATGGTTCCTTCTCATGTACTTTCCAAAATGCTGGGGATTACTTATGTCGTAGTGGTCTTTCTTTC
GATAGTACTAAGACCCCATCTCAAATTGGTCGTATGAAGGCTGATTTCAAACTTGTCAAACAAAAT
AGTTCCAATGTTGGTTATTCCTATGTTGGTGTTTACGGTTGGACTAGAAGTCCACTTGTCGAATACT
ACATTGTCGATAATTGGCTTAGTCCATTCCCACCAGGTGATTGGGTTGGTAACAAGAAGTTTGGTT
CTTTCACTATTGATGGTGCTCAATACACTGTTTATGAAAACACTCGTACTGGTCCATCTATTGATGG
TGATACCACCTTCAATCAATACTTTAGTATTCGTCAACAAGCTCGTGATTGTGGTACCATTGATATT
TCTGCTCACTTTGATCAATGGGAAAAGCTTGGTATGACTATGGGTAAATTACATGAAGCCAAGGTT
TTAGGTGAAGCCGGTAACGTTAACGGTGGTGCCAGTGGTACCGCTGATTTCCCATACGCAAAGGTT
TACATTGGTGATTAG

Figure 4C

Xylanase G3P protein SEQ ID NO:5

QSFCSSASHSGQSVKVTGNKVGTIGGWGYELWADSGNNSATFYSDGSFSCTFQNAGDYLCRSGLSFDS
TKTPSQIGRMKADFKLVKQNSSNVGYSYVGVYGWTRSPLVEYYIVDNWLSPFPPGDWVGNKKFGSFT
IDGAQYTVYENTRTGPSIDGDTTFNQYFSIRQQARDCGTIDISAHFDQWEKLGMTMGKLHEAKVLGEA
GNVNGGASGTADFPYAKVYIGD

N.A. encoding Xylanase G3P protein SEQ ID NO:6

CAAAGTTTCTGTAGTTCAGCTTCTCACTCTGGACAAAGTGTAAAGGTAACCGGCAACAAGGTTGG
AACTATTGGTGGTTGGGGTTACGAATTATGGGCTGATAGTGGTAATAACAGTGCTACTTTCTATTC
TGATGGTTCCTTCTCATGTACTTTCCAAAATGCTGGGGATTACTTATGTCGTAGTGGTCTTTCTTTC
GATAGTACTAAGACCCCATCTCAAATTGGTCGTATGAAGGCTGATTTCAAACTTGTCAAACAAAAT
AGTTCCAATGTTGGTTATTCCTATGTTGGTGTTTACGGTTGGACTAGAAGTCCACTTGTCGAATACT
ACATTGTCGATAATTGGCTTAGTCCATTCCCACCAGGTGATTGGGTTGGTAACAAGAAGTTTGGTT
CTTTCACTATTGATGGTGCTCAATACACTGTTTATGAAAACACTCGTACTGGTCCATCTATTGATGG
TGATACCACCTTCAATCAATACTTTAGTATTCGTCAACAAGCTCGTGATTGTGGTACCATTGATATT
TCTGCTCACTTTGATCAATGGGAAAAGCTTGGTATGACTATGGGTAAATTACATGAAGCCAAGGTT
TTAGGTGAAGCCGGTAACGTTAACGGTGGTGCCAGTGGTACCGCTGATTTCCCATACGCAAAGGTT
TACATTGGTGATTAG

XYLANASE VARIANTS AND METHODS

SEQUENCE LISTING SUBMISSION VIA EFS-WEB

A computer readable text file, entitled "SequenceListing.txt" created on Dec. 6, 2021 with a file size of 24,123 bytes contains the sequence listing for this application and is hereby incorporated by reference in its entirety.

FIELD OF THE INVENTION

This invention relates to the variant xylanase enzymes, polynudeotides encoding the variant xylanase enzymes, methods of producing the variant xylanase enzymes, and methods of using the variant xylanase enzymes. Also described are the use of variant xylanases of the invention in the animal feed industry. The invention also relates to compositions comprising one or more variant xylanases of the invention.

BACKGROUND OF THE INVENTION

Xylan is a complex heteropolysaccharide consisting of different monosaccharides such as L-arabinose, D-galactose, D-mannoses and organic acids such as acetic acid, ferulic acid, glucuronic acid interwoven together with help of glycosidic and ester bonds. The breakdown of xylan is restricted due to its heterogeneous nature and it can be overcome by xylanases which are capable of cleaving the heterogeneous β-1,4-glycoside linkage. Xylanases are abundantly present in nature (e.g., molluscs, insects and microorganisms) and several microorganisms such as bacteria, fungi, yeast, and algae are used extensively for its production. (Bhardwaj N. et al. Bioresources and Bioprocessing (2019) 6:40, 1-36, hereby incorporated by reference in its entirety)

Natural xylanase enzymes, such as that of the fungus *Trichoderma reesei*, have been added to animal feed to increase the efficiency of digestion and assimilation of nutrients. During digestion of feed grains such as wheat and barley, non-starch polysaccharides, including xylan, increases the viscosity of the digesta in the absence of added exogenous enzyme. This interferes with the diffusion of the digestive enzymes to the feed and the subsequent assimilation of the nutrients. The highly viscous digesta increases the occurrence of sticky stool, which increases the likelihood of disease and causes effluent run-off problems. The addition of xylanase in feed breaks down the xylan and decreases the viscosity of the digesta, thereby increases the digestibility and nutritive value of poorly degradable feeds such as barley and wheat. (U.S. Pat. No. 7,060,482 B1, U.S. Patent Application Publication US 2008/0020088 A1, hereby incorporated by reference in their entireties).

Animal feeds are usually pelleted at high temperatures for sterilization against harmful bacteria, for example, *Salmonella*. Feed pelleting is carried out by heating the feed solids with 100 to 140° C. steam and passing them through an extruder/pelletingauger to form feed pellets, which then cool in a storage bin. The overall resulting temperature within the solids, prior to, during, and after pellet formation reaches about 70-95° C., for up to 30 min. It is desirable to add the xylanase during the feed pelleting process. This would save the feed formulators the additional step of adding liquid xylanase, which is inconvenient and can introduce microbial contamination into the feed. The option of adding solid xylanase as a separate step is also undesirable, as the solids would not be evenly mixed (U.S. Pat. No. 7,060,482 B1, hereby incorporated by reference in its entirety). However, the high temperature during this feed pelleting process usally inactivates the enzyme.

Selle and Ravindran laid out the characteristics for an ideal feed enzyme, namely: 1) a high specific activity per unit of protein, 2) good thermostability during feed processing, 3) high activity in the typical pH range of the animal gut, 4) resistance to gastric proteases, and 5) good stability under ambient temperatures. (SELLE, P. H. and RAVINDRAN, V. (2007) Microbial phytase in poultry nutrition. Animal Feed Science and Technology 135: 1-41, hereby incorporated by reference in its entirety). Even though currently available enzymes are beneficial for use as feed additives, new enzymes exhibiting high activity and resistance to heat treatment and/or low pH in the gut are also desired.

It is an object of the present invention to provide xylanase variants having xylanase enzyme activity with increased total activity, specific activity, temperature activity, pH activity, total stability, thermostability, and/or pH tolerance, and polynudeotides encoding the xylanase variants and methods of using the xylanase variants in animal feed industry.

BRIEF SUMMARY OF THE INVENTION

Accordingly, the present invention provides (variant) xylanases and methods of producing and using them. The amino acid sequence numbers and nucleic acid sequence numbers of the present invention are listed in Table 1.

TABLE 1

Amino acid sequence numbers and nucleic add sequence numbers.

| | |
|---|---|
| Xylanase G1P (wild-type) protein | SEQ ID NO: 1 |
| Xylanase G2P protein | SEQ ID NO: 3 |
| Xylanase G3P protein | SEQ ID NO: 5 |
| N.A. encoding Xylanase G1P (wild-type) protein | SEQ ID NO: 2 |
| N.A. encoding Xylanase G2P protein | SEQ ID NO: 4 |
| N.A. encoding Xylanase G3P protein | SEQ ID NO: 6 |

In one aspect, the invention provides a composition comprising a variant xylanase enzyme comprising at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, and wherein said variant enzyme is at least 90% identical to SEQ ID NO:1.

In a further aspect, the invention provides a composition comprising a variant xylanase enzyme comprising at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant xylanase enzyme has at least 1.1 fold better activity as compared to SEQ ID NO:1 under a condition selected from the group consisting of total activity at about 75° C., total activity at about 80° C., total activity at about 85° C., total activity at about 90° C., and total activity at about 95° C.; and wherein said variant xylanase enzyme is at least 90% identical to SEQ ID NO:1.

In an additional aspect, the invention provides a composition comprising a variant xylanase enzyme comprising at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant xylanase enzyme has at least 1.1 fold better activity as compared to SEQ ID NO:1 under a condition selected from the group consisting of tolerance against pH 2.5, tolerance against pH 3.0, tolerance against pH 3.5, tolerance against pH 4.0, tolerance against pH 4.5, tolerance against pH 5.0, tolerance against pH 5.5, tolerance against pH 6.0, and tolerance against pH 6.5; and wherein said variant xylanase enzyme is at least 90% identical to SEQ ID NO:1.

In a further aspect, the invention provides a composition comprising a variant xylanase enzyme exhibiting at least 95%, 96%, 97%, 98%, or 99% identity to SEQ ID NO:1.

In an additional aspect, the invention provides a composition comprising a variant xylanase enzyme comprising at least one amino acid substitution as compared to SEQ ID NO:1 as described herein, wherein said amino acid substitution(s) occur at one of said positions, two of said positions, three of said positions, four of said positions, five of said positions, six of said positions, seven of said positions, eight of said positions, nine of said positions, ten of said positions, or eleven of said positions.

In a further aspect, the invention provides a composition comprising a variant xylanase enzyme comprising at least one amino acid substitution as compared to SEQ ID NO:1 as described herein, wherein said amino acid substitution(s) is selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V27I, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, H131F, H131P, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In an additional aspect, the invention provides a composition comprising a variant xylanase enzyme comprising at least one amino acid substitution as compared to SEQ ID NO:1 as described herein, wherein said amino acid substitution(s) is selected from the group consisting of S5I, T51C, K15T, G25E, S5K, T51E, K20C, T51R, Q1P, T51Q, S8C, K20V, Q12T, G26C, S8H, K20S, K15R, Q12L, S6K, Q1H, S8R, K15H, S5R, G26T, G26N, K15V, S6T, S6H, G26R, V27W, T149R, G224K, D225Y, N160Q, T190P, G224L, G224M, G224T, Q168S, N160K, T190H, N160R, S105D, G56R, S90I, F120Y, N54D, S89C, F120H, G56T, S90C, S105H, V99A, G56H, S89V, S133L, S90E, V99G, S133T, S90A, S90F, S133K, N54G, S89A, G93L, F120D, S89T, S105I, S105N, H131F, P121G, F120S, H131P, G56K/P119Q G56K/F120Y/S133D, G56K/S178T, T51S/S133D, V27I/G56K/N160K, P121R/S133D/N160K, G18S/V27I/G56K/N160K/L194M, G18S/N160K, G18S/G28D, G56K/P119Q/P121R/S133D/L194M, G18S/G56K/F120Y, V27I/N160K, T51S/P119Q/S133D/N160K/S178T, G18S/T23S/G56K/P119Q/F120Y/P121R/S133D, T51S/F120Y, G56K/S133D/N160K, T51S/G56K/F120Y/S178T, G56K/N160K, T51S/G56K/S133D/N160K, T51S/P119Q/F120Y/N160K, Q1P/S8R/K20V/T51C/S89C/S90H, Q1P/S8H/K20V, Q1P/K15T/K20C/V27W/V99A, S8C/K20V/V27W/H131F, S8H/H131F, V27W/H131F, Q1P/K20C/V27W, K15T/K20V/V27W, K20C/V27W/S89V/S90H, Q1P/S8H/K15T/V27W/H131F, Q1P/S8C/K15T/K20V/V27W/S89T/H131F, Q1P/S8H/K15H/V27W/H131F, Q1P/S8H/V27W/S89T, Q1P/S8R/S89A/S90H/H131F, K20V/V27W/T51C/S89C/S90H/H131F, Q1P/H131F, K15H/K20V/V27W/H131F/G224K, Q1P/S8R/K15T/K20V/V27W/S89A/S90H/V99A/H131F/G224L, Q1P/S8H/T51C/H131F, Q1P/K20V/V27W/V99A/H131F, Q1P/S8R/K20V/V27W/T51C/G224L, Q1P/S8R/K15T/K20C/V27W/S89A/H131F, K15T/K20V/V27W/H131F, Q1P/S8R/K20C/V27W, S8H/K20V/V27W, Q1P/S8H/K15H/K20V/V27W/S89C/S90H/V99A/H131F, Q1P/S8R/K15H/V27W/V99A, K15H/V27W, S90E/H131F, Q1P/K15H/K20V/V27W/T51C/S90H/H131F, K15T/K20C/V27W/H131F, V27W/G224L, K20V/V27W/H131F, K15T/K20V/V27W/T51C/G224L, Q1P/S8C/H131F, Q1P/S8R/K15H/K20V/V27W/T51C/S90E, Q1P/S8R/V27W, Q1P/S8C/V27W/T51C/H131F, Q1P/S8H, K15T/K20C/V27W/S90H/H131F, K15T/V27W/S90H, Q1P/K20V/H131F, K15T/V27W, Q1P/H131F/G224L, S8C/K15T/K20V/V27W/T51C/S90H, Q1P/K15T/K20C/V27W/T51C/S89C/S90H/H131F, Q1P/S8H/K20C/V27W, Q1P/S90H/N160K/T190H, Q1P/S5K/G26N/V27W/F120Y/Q168S/T190H, Q12T/K20C/G26T/S89C/H131F/Q168S, S5I/K20S/S89T/V99A/F120D/H131F/Q168S/T190H, Q1P/S5K/K20S/S89C/F120Y, S6H/G56K/V99A/Q168S/T190H, S8R/K20V/T190H, K15T/G26T/G56K/H131F/N160K/T190H, S8H/K20C/S105N/H131F/N160Q/Q168S, Q1H/S5R/K15V/G56K/Q168S, K20S/G56K/F120Y/N160Q/T190H, S8R/H131F/T190H, G26N/V27W/G56K/S90H/H131F/Q168S/T190H, S89V/H131F/Q168S, S5R/Q12L/K15T/G26N/V27W/G56K/F120Y/H131F, S6H/S8R/K20S/S89A/V99A, Q1P/S5R/G26T/S90C/H131F/Q168S/T190H, S8H/K20C/T51R/S89A/P121R/N160K/T190H, Q1P/S5R/Q12T/K15V/G26T/V27W/S90E/H131F/G224K, Q1P/S5R/K20S/G56K/S89C/H131F/N160K/Q168S/T190H, Q1H/S5K/Q12L/S90H/S105N/T190H, S8C/K20C/T51C/S89A/Q168S, G26N/V27W/S105N/Q168S/G224L, S5I/S90H/S105N/F120Y/P121R/H131F/Q168S/G224K, S6H/S8C/K20S/T51S/F120Y/P121R/T190H, S5K/V99G/T190H, S5K/K20V/G56K/H131F/Q168S, S8R/T51R/S89T/H131F/T190H, Q1P/S5R/S8R/V99A/N160Q, S8R/T51C/F120D/Q168S/G224L, Q1P/V27W, Q1P/Q12T/K20V/G56K/S105N/N160Q/T190H/G224K, Q1H/S5I/Q12L/K15R/H131F, S89C/F120D/H131F/N160Q/G224L, K20C/P121R, K20S/V27W/T51Q/S105N/F120D/P121R/N160Q/T190H/G224M, Q1H/S8C/K20V/G56K/S89A/H131F/T190H/G224L, S8H/G26T, S6H/S8C/K20S/S89C/T190H, K20S/T51C/S89V/T190H, Q1H/Q12L/K15R/V27W/G56K/V99A/N160K/T190H, S8C/K15R/S105N/H131F/T190H, Q1H/S5R/Q12L/K20C/G56K/H131F/T190H, Q1H/S5I/Q12T/K15V/G26T/G56K/S90E/S105N/Q168S, S6H/K20C/S89T, Q1H/S5R/K15R/G26N/G56K/H131F/T190H/G224K, S89V/V99G/T190H, Q1H/S5I/Q12L/K15T/Q168S, Q12L/K15R/S90H/H131F/Q168S/T190H, Q1H/S5I/T190H, Q1P/S8H/K20V/T51Q/S89T/V99A/F120D/T190H, S8R/K20S/G56K/K86T/S89A/V99A/H131F, S8C/Q12T/K15V/G56K/T190H, K20S/S89C/F120Y/H131F/T190H, Q1P/K20V/G56K/S90E/S105N/H131F, S5I/K20S/G26N/V27W/G56K/S90H/S105N/Q168A/T190H, Q1P/S2K/S6H/S8R/S105N/Q168S/G224K, S8H/K20C/T51R/S89A/N160K/Q168S, Q1H/S5R/Q12T/K15R/G26N/S89A/V99G/F120D/P121R/T190H/G224M, S8C/K20S/G56K/S89C/V99G/F120D/P121R/T190H/G224, S6H/S8H/K20C/T51R/S89A/P121R/T190H, Q1P/S5K/T51Q/V99G, Q1P/S5I/S89V/S105N/H131F/Q168S, S8H/K15V/K20C/T51Q/S89A/S105N/Q168S, Q1P/S5I/K15R/G26T/S89C/V99G/

F120Y/N160Q/T190H/G224K, S89C/H131F/Q169S/ T190H, Q1P/S5K/Q12L/K20C/T51Q/S89V/F120Y/ N160K/Q168S/T190H, Q1H/S5K/G56K/F120D/P121R/ Q168S, T51E/V99A/P121R/H131F/N160Q/Q168S/T190H/ G224K, Q1P/S5R/Q12T/K15H/G26N/V27W/G56K/S90C/ S105N/T190H, S6H/S8R/K20C/T51C/F120D/T190H, S8R/ K20S/F120D/P121R, S5R/S105N/Q168S/T190H, Q1H/ S5R/K15V/G26N/V27W/H131F/Q168S/T190H, Q1H/ S5R/Q12L/K15T/S90E/S105N/H131F/Q168S, K20V/ S89V/V99A/N160K/Q168S/G224K, S90C/S105N/H131F, S6H/S8H/K20V/T190H, S8H/T51E/V99G/Q168S/T190H, S5R/Q12L/K20V/S89C/Q168S/T190H, Q1P/S5K/Q12T/ K15H/G26N/V27W/G56K/S89C/H131F, K15R/G56K/ T190H, Q1H/S5K/Q12T/K15T/G26T/G56K/S89C/H131H/ N160K/Q168S, S6H/S8R/K20V/T51E/S90H/S105N/ H131F/T135S/Q168S/T190H, Q1P/S5K/Q12L/K15R/ G56K/S89T/F120D, Q12L/H131F/N160K/T190H, Q1H/ S5R/Q12T/K15H/G26N/V27W/G56K/H131F, Q1P/S5K/ Q12T/G56K/S105N/H131F/Q168S/T190H/G224L, V27W/ S90C/V99G/S105N/F120Y/N160K/Q168S, G56K/S90C/ H131F/Q168S/T190H, Q1P/S5R/G26T/G56K/S105N/ H131F/Q168S/T190H, S8C/T51E/S89A/V99A/H131F/ Q168S/T190H, S5K/K15H/G26T/S90H/H131F, G26N/ G56K/S89T/H131F/Q168S/T190H/G224K, Q1P/Q12L/ K15T/G26N/V27W/S90H/S105N/H131F/T190H, G56K/ S90C, K20S/S89V/V99G/S105N/T190H, S5I/G26N/G56K/ V99G/S105N, Q1P/S5R/G56K/H131F/N160K/T190H, Q1H/S5I/K20V/S89C, K20C/T51Q/S89C/V99G/F120D/ P121R/T190H, S8R/Q12T/K15V/T51R/S89A/V99A/ F120D/P121R/T190H, G26N/V27W/S105N/H131F/ Q168S, S6H/S89T/V99A/F120D/P121R/N160Q/Q168S/ T190H, T51Q/H131F, Q1P/S5R/Q12L/K15V/V27W/ G56K/V99A/S105N/F120D/N160Q/Q168S, Q1P/S5R/ G26N/G56K/S90H/S105N/F120D/P121R/T190H, S5R/ Q12T/K20V/G56K/F120Y, S105N/F120D/P121R/T190H, S8R/K20C/G26N/V27W/G56K/H131F/T190H, Q1H/ V27W/G56K/S90C, G56K/S90C/H131F/Q168S/T190H, Q12L/K15R/V27W/G56K/S90E, Q1H/S105N/T190H, G56K/S89T/S105N/P121R/H131F/Q168S/G224K, K20S/ S89A/V99G/S105N/N160Q/T190H, Q1P/P121R/H131F/ N160Q/T190H, K15V/T51Q/S89V/H131F/G224H, Q1P/ K20S/N160K/T190H, S8H/G56K/S89V/F120Y/P121R/ N160Q/Q168S/T190H, Q1H/S5K/V27W/G56K/Q168S/ T190H, F120D/P121R/Q168S, S8H/K20V/T51S/V99A/ T190H, S8R/T51E/S89T/V99G/N160K/T190H, K20S/ S89C/T190H, K20S/S90E/G224M, K15V/G56K/S89T/ T190H, S6H/S8R/Q12L/K15V/G26T/V27W/G56K/Q168S, Q1P/S5I/K20S/G56K/S90E/H131F/Q168S, S6H/F120Y/ T190H, S8H/K20V/T51S, S105N/H131F, S5I/Q12T/K15H/ G26T/V27W/G56K/S90H/S105N/H131F/N160K/T190H, Q1H/S5R/G26T/G56K/S105N/H131F/G224K, S5I/S89C/ S105N/H131F/Q168S, Q1P/S5R/Q12L/K15R/G56K/S90H/ F120D/P121R/H131F/N160K, S105N/H131F/Q168S, S6H/ S8R/K20V/G56K/F120D/P121R/H131F/T190H, Q1P/S5I/ G26N/V27W/S90E/H131F/Q168S/G224M, G56K/T190H, S8R/K20C/T51E/S89V/Q168S/G224M, S8C/K20S/S89A/ F120Y/P121R/N160Q, S5R/S89T/F120Y/P121R/T190H, G26N/V27W/G56K/S105N/H131F/Q168S, S6H/S8R/ S89A/F120Y, Q1P/S5R/Q12L/K15R/G26T/S90H/Q158S/ T190H, K20C/H131F, K20C/V27W/H131F, K15H/K20C/ H131F, K15H/K20V/V27W/S89A/H131F, K15H/S89C/ H131F, K15H/V27W/H131F, K15R/K20C/H131F, K15R/ K20C/S89A/H131F, K15R/K20C/S89C/H131F, K15R/ K20C/S89V/H131F, K15R/K20V/H131F, K15R/S89A/ H131F, K15R/S89C/H131F, K15R/S89V/H131F, K20C/ H131F, K20C/S89T/H131F, K20C/V27W/S89T/H131F/ E185K, K20V/H131F, K20V/S89C/H131F, K20V/S89T/ H131F, K20V/S89V/H131F, S89A/H131F, S89C/H131F, S8C/K15H/K20C/S89T/H131F, S8C/K20C/H131F, S8C/ K20V/S89C/H131F, S8C/K20V/S89T/H131F, S8H/K15R/ K20C/S89T/H131F, S8H/K20C/S89T/H131F, S8H/K20C/ V27W/H131F, S8H/K20V/H131F, S8H/K20V/S89C/ H131F, S8H/K20V/V27W/S89T/H131F, S8R/K15H/K20V/ S89C/H131F, S8R/K15R/K20C/H131F, S8R/K20C/S89C/ H131F, V27W/S89C/H131F, V27W/S89T/H131F, G26T/ V27W/H131F, V27W/S89A/H131F, V27W/H131F/S133T, G26T/V27W/S89A/H131F, G26T/V27W/H131F/S133T, V27W/S89A/H131F/S133T, G26T/V27W/S89A/H131FS/ S133T, G26T/V27W/S35R/S89A/H131FS/S133R, and V27W/N38Y/F52W/G56Y/H131F/G201L.

In a further aspect, the invention provides a composition comprising a variant xylanase enzyme as described herein, wherein said variant xylanase enzyme has at least 95% sequence identity to the amino acid sequence of SEQ ID NO:3 or SEQ ID NO:5.

In a further aspect, the invention provides a composition comprising a variant xylanase enzyme comprising at least one amino acid substitution as compared to SEQ ID NO:1 as described herein, wherein said amino acid substitution is H131F.

In an additional aspect, the invention provides a composition comprising a variant xylanase enzyme comprising at least one amino acid substitution as compared to SEQ ID NO:1 as described herein, wherein said amino acid substitutions are V27W/H131F.

In a further aspect, the invention provides a composition comprising a variant xylanase enzyme comprising an amino acid substitution H131F, and further comprising at least one amino acid substitution selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V27I, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In a further aspect, the invention provides a composition comprising a variant xylanase enzyme comprising amino acid substitutions V27W/H131F, and further comprising at least one amino acid substitution selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In an additional aspect, the invention provides a nucleic acid encoding the variant xylanase enzyme as described herein.

In a further aspect, the invention provides the nucleic acid as described herein, wherein the nucleic acid is codon optimized for a host organism for expression of the variant xylanase enzyme as described herein in said organism.

In an additional aspect, the invention provides the nucleic acid as described herein, wherein the nucleic acid comprises a sequence that has at least 80% sequence identity to the sequence of SEQ ID NO:4 or SEQ ID NO:6.

In a further aspect, the invention provides the nucleic acid as described herein, wherein the nucleic acid comprises the sequence of SEQ ID NO:4 or SEQ ID NO:6.

In a further aspect, the invention provides an expression vector comprising the nucleic acid as described herein.

In an additional aspect, the invention provides a host cell comprising the nucleic acid as described herein.

In a further aspect, the invention provides a host cell comprising the expression vector as described herein.

In an additional aspect, the invention provides the host cell as described herein, wherein said host cell is selected from the group consisting of a bacterial cell, a fungal cell, and a yeast cell.

In a further aspect, the invention provides a method of making a variant xylanase enzyme comprising: a) culturing the host cell as described herein under conditions wherein said variant xylanase enzyme is expressed; and b) recovering said variant xylanase enzyme.

In an additional aspect, the invention provides a composition comprising the variant xylanase enzyme as described herein and further comprising animal feed.

In a further aspect, the invention provides a formulation suitable for consumption by an animal, wherein said formulation comprises the variant xylanase enzyme as described herein and one or more consumable components.

In a further aspect, the invention provides a method of preparing animal feed comprising adding the variant xylanase enzyme as described herein to said animal feed to produce a xylanase-animal feed combination, and heat sterilizing said xylanase-animal feed combination.

In an additional aspect, the invention provides the method of preparing animal feed as described herein, wherein said animal feed is a poultry or swine feed.

BRIEF DESCRIPTION OF THE DRAWINGS

FIGS. 1A-1N display the pH 5.5 and low pH activities, and low pH and 90° C. stability of xylanase variants as described in Examples 3-5. Xylanase variants are described as a comparison to G1P xylanase: -- indicates 0.8 fold or less (a detrimental effect), - indicates 0.8-1.1 fold (a neutral effect), + indicates 1.1-1.6 fold (a positive effect) and ++ indicates >1.6 fold (a very positive effect). For CL00118607-CL00123961 (except CL00122441) were screened at pH 2.5 for low pH activity and pH 3 for all others. For CL00118607-CL00135705, CL00128404, CL00131244, and CL00131369 in thermostability experiments, these variants were incubated for 15 min at 90° C., while all other variants were incubated for 5 min. Values left blank indicate these variants were not assayed under that condition.

FIG. 2 displays the pH 5.5 and pH 3 activities and 90° C. thermostability of xylanase variants as described in Examples 3-5. Variants are described as a comparison to G2P xylanase: -- indicates 0.8 fold or less (a detrimental effect), - indicates 0.8-1.1 fold (a neutral effect), + indicates 1.1-2.5 fold (a positive effect) and ++ indicates >2.5 fold (a very positive effect). All variants were assayed at pH 3 for low pH activity and incubated for 5 min at 90° C. for thermostability assays.

FIGS. 3A and 3B display particular variants of xylanase G1P by position that demonstrate beneficial properties in low pH activity, pH 5.5 activity, low pH stability, or thermostability as displayed in FIGS. 1 and 2.

FIG. 4A provides the amino acid sequence (SEQ ID NO:1) of Xylanase G1P (wild-type) protein, and the nucleic acid sequence (SEQ ID NO:2) encoding the Xylanase G1P (wild-type) protein. FIG. 4B provides the amino acid sequence (SEQ ID NO:3) of Xylanase G2P protein, and the nucleic acid sequence (SEQ ID NO:4) encoding the Xylanase G2P protein. FIG. 4C provides the amino acid sequence (SEQ ID NO:5) of Xylanase G3P protein, and the nucleic acid sequence (SEQ ID NO:6) encoding the Xylanase G3P protein. Performance improvements of these variants are displayed in FIGS. 1 and 2.

DETAILED DESCRIPTION OF THE INVENTION

I. Introduction

Xylans form the major component of hemicellulose in plant biomass. Xylan is a heteropolysaccharide substituted with monosaccharides such as L-arabinose, D-galactose, D-mannoses and organic acids such as acetic acid, ferulic acid, glucuronic acid interwoven together via glycosidic and ester bonds. The backbone of xylans consists of a chain of β-1,4-linked xylopyranoside residues. The breakdown of xylan is restricted due to its heterogeneous nature, and it can be overcome by xylanases which are capable of cleaving the heterogeneous β-1,4-glycoside linkage (Bhardwaj N. et al. Bioresources and Bioprocessing (2019) 6:40, 1-36; U.S. Patent Application Publication US 2008/0020088 A1, hereby incorporated by reference in their entireties).

Xylanases play an important role in animal feed by breaking the feed ingredient arabinoxylan, decreasing the content of non-starch polysaccharides and reducing the raw material viscosity. Therefore, xylanases improve the utilization of proteins and starch present in the feed and increase the digestibility and nutritive value of poorly degradable feeds such as barley and wheat (Bhardwaj N. et al. Bioresources and Bioprocessing (2019) 6:40, 1-36; U.S. Pat. No. 7,060,482 B1; U.S. Patent Application Publication US 2008/0020088 A1, hereby incorporated by reference in their entireties).

Increasingly, animal feeds are pelleted at high temperatures for sterilization by heating the feed solids with 100 to 140° C. steam and passing them through an extruder/pelletingauger to form feed pellets, which then cool in a storage bin. The overall resulting temperature within the solids, prior to, during, and after pellet formation reaches about 70-95° C. (U.S. Pat. No. 7,060,482 B1, hereby incorporated by reference in its entirety). Accordingly, variant xylanase enzymes that exhibit thermostability, and/or high activity at or near physiological pH and temperature are desired and provided herein.

II. Definitions

By "protein" herein is meant at least two covalently attached amino acids, which includes proteins, polypeptides, oligopeptides, and peptides. The peptidyl group generally comprise naturally occurring amino acids and peptide bonds. In addition, polypeptides may include synthetic derivatization of one or more side chains or termini, glycosylation, PEGylation, circular permutation, cydization, linkers to other molecules, fusion to proteins or protein domains, and addition of peptide tags or labels.

By "amino acid" and "amino acid identity" as used herein is meant one of the 20 naturally occurring amino acids that are coded for by DNA and RNA.

By "position" as used herein is meant a location in the sequence of a protein. In most cases unless stated otherwise, the position number (which is more fully discussed below) is relative to the first amino acid of the mature xylanase sequence, e.g. excluding the signal peptide.

The phrase "mature polypeptide" means a polypeptide in its final form excluding the signal peptide and following translation and any post-translational modifications, such as N-terminal processing, C-terminal truncation, glycosylation, phosphorylation, etc.

The phrase "mature polypeptide coding sequence" refers to a polynucleotide that encodes a mature polypeptide having xylanase activity.

By "residue" as used herein is meant a position in a protein and its associated amino acid identity. For example, Serine 133 (also referred to as Ser133 or S133) is a residue at position 133 in the xylanase G1P parental enzyme.

The term "wild-type" xylanase refers to the sequence of the typical form of a xylanase as it occurs in nature, such as molluscs, insects and microorganisms found in nature.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize xylanase G1P (wild-type) protein as set forth in SEQ ID NO:1 as the parent polypeptide.

The term "parent" or "parent xylanase" refers to a xylanase to which an alteration is made to produce the variant xylanases of the present invention. The parent may be a naturally occurring (wild-type) polypeptide or a variant or fragment thereof. In some embodiments, the parent polypeptide of the present invention is SEQ ID NO:1. In some embodiments, the parent polypeptide of the present invention is SEQ ID NO:3. In some embodiments, the parent polypeptide of the present invention is SEQ ID NO:5.

The term "variant" refers to a polypeptide having xylanase activity and comprising an alteration or a modification, e.g., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

By "variant protein" or "protein variant", as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about twenty amino acid modifications, and preferably from about one to about eleven amino acid modifications compared to the parent. As described below, in some embodiments the parent polypeptide is a wild-type sequence. As further discussed below, the protein variant sequence herein will preferably exhibit at least about 90% sequence identity with a parent protein sequence, and most preferably at least about 95% sequence identity, more preferably at least about 96%, 97%, 98% or 99% sequence identity. Variant protein can refer to the variant protein itself, compositions comprising the protein variant, or the DNA sequence that encodes it. Thus, by "variant xylanase" or "xylanase variant" herein is meant a novel xylanase that has at least one amino acid modification in the amino acid sequence as compared to a parent xylanase enzyme. As discussed herein, in some cases the parent xylanase is a second or higher generation of a variant xylanase, such as xylanase G2P protein (SEQ ID NO:3) or G3P protein (SEQ ID NO:5). Unless otherwise noted or as will be obvious from the context, the variant xylanases of the invention generally are compared to the G1P sequence (SEQ ID NO:1). Additionally, unless otherwise noted, the variant xylanases of the invention are enzymatically active, that is, there is detectable xylanases activity using the xylanases assay described in Examples below.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution G28D refers to a variant polypeptide, in this case a xylanase, in which the glycine at position 28 is replaced with aspartic acid. Multiple mutations are separated by forward slash marks ("/"), e.g., "G56K/F120Y/S133D" representing substitutions at positions 56, 120 and 133, respectively (in some cases a "+" can be used). For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −133E or 133E designates an insertion of glutamic acid after position 133 and before position 134. Additionally, −133ADE or 133ADE designates an insertion of AlaAspGlu after position 133 and before position 134.

By "amino acid deletion" or "deletion" as used herein is meant the removal of an amino acid sequence at a particular position in a parent polypeptide sequence. For example, Q12− or Q12#, Q12 ( ) or Q12del designates a deletion of glutamine at position 12. Additionally, QSV12− or QSV12# designates a deletion of the sequence GlnSerVal that begins at position 12.

The term "fragment" means a polypeptide having one or more (e.g., several) amino acids absent from the amino and/or carboxyl terminus of a mature polypeptide. A "xylanase fragment" herein means a portion of an amino acid sequence depicted herein that maintains xylanase activity. In one aspect, a xylanase fragment contains at least 50, at least 100, at least 150, at least 200, at least 210 or at least 220 amino acid residues of a mature xylanase polypeptide having zero, one or more of the substitutions according to the invention.

By "non-naturally occurring modification" as used herein is meant an amino acid modification that is not found in the wild-type enzyme.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Identification of the corresponding amino acid residue in another xylanase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 51 1-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), EMBOSS EMMA employing ClustalW (1.83 or later; Thompson et al., 1994, Nucleic Acids Research 22: 4673-4680), and EMBL-EBI employing Clustal Omega (Sievers and Higgins, 2014, Methods Mol Biol. 2014; 1079:105-16), using their respective default parameters.

When the other enzyme has diverged from the polypeptide of SEQ ID NO:1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The standardly accepted IUPAC single letter or three letter amino acid abbreviation is employed and shown in Table 2.

For an amino acid substitution, the following nomenclature is used herein: Original amino acid, position, substituted amino acid. Accordingly, the substitution of glycine at position 28 with aspartic acid is designated as "Gly28Asp" or "G28D". Multiple mutations are separated by forward slash marks ("/"), e.g., "G56K/F120Y/S133D", representing substitutions at positions 56, 120 and 133, respectively.

TABLE 2

Three-letter abbreviations, one-letter abbreviations and names of the 20 amino acids.

| 3 - letter Abbreviation | 1 - letter abbreviation | Amino acid name |
| --- | --- | --- |
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |

The term "xylanase" or "xylanases" refers to one or more enzymes selected from the group consisting of endo-1,4-β-D-xylanases (EC 3.2.1.8), β-D-xylosidases (E.C.3.2.1.37), α-glucuronidase (EC 3.2.1.139), acetylxylan esterase (EC 3.1.1.72), α-L-arabinofuranosidases (E.C.3.2.1.55), p-coumaric esterase (3.1.1.B10) and ferulic acid esterase (EC 3.1.1.73) involved in the depolymerization of xylan into simple monosaccharide and xylooligosaccharides. For purposes of the present invention, xylanase activity is determined according to the procedures described in the Examples herein, for example, the Xylanase Enzymatic Assay to determine the xylanase activity in Examples 3-5.

The term "coding sequence" refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a xylanase of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a polypeptide, protein or preprotein described herein, including, but not limited to, transcription, post-transcriptional modification, translation, post-translational modification, and secretion.

The term "preprotein" refers to a protein precursor that is an inactive protein or peptide and contains a signal peptide sequence. The preprotein can be turned into a protein in an active form by post-translational modification, such as cleaving off the signal peptide.

The term "expression vector" refers to a linear or circular DNA molecule that comprises a polynucleotide encoding a polypeptide, protein or preprotein as described herein, and is operably linked to control sequences that provide for its expression.

The term "subsequence" refers to a polynudeotide having one or more (e.g., several) nucleotides absent from the 5'- and/or 3'-end of a mature polypeptide coding sequence; wherein the subsequence encodes a fragment having xylanase activity.

By "recombinant enzyme" herein is meant that the enzyme is produced by recombinant techniques and that nucleic acid encoding the variant enzyme of the invention is operably linked to at least one exogeneous (e.g. not native to the parent phytase) sequence, including, for examples, promoters, terminators, signal sequences, etc., as are more fully outlined below.

The term "host cell" refers to any cell type that is susceptible to transformation, transfection, transduction, or the like with a nucleic acid construct or expression vector comprising a polynucleotide of the present invention, and that allows for expression of the enzyme. The term "host cell" encompasses any progeny of a parent cell that is not identical to the parent cell due to mutations that occur during replication. In many embodiments, the xylanases of the invention (including both the xylanase and variant enzymes described herein) are not produced in the endogeneous host.

The term "improved property" refers to a characteristic associated with a variant xylanase enzyme described herein that is improved compared to the parent xylanase enzyme. Such improved properties of xylanases include, but are not limited to, increased total activity, increased specific activity (e.g. the catalytic activity, its ability to bind to xylan, and/or its cellulolytic/hydrolytic activity), increased temperature activity (e.g., increased activity at a broad range of temperatures including high temperatures), increased pH activity (e.g., increased activity at a broad range of pH including low pH), increased total stability, increased temperature stability (e.g., increased stability against a broad range of temperatures including high temperatures), and increased pH stability (e.g., increased stability against a broad range of pH including low pH), formulation stability (including liquid, solid and pellets), protease stability, performance in the feed pelleting process, performance in animals and/or animal feed and/or protease stability, etc.

The term "nucleic acid construct" refers to a nucleic acid molecule, either single-stranded or double-stranded, which is isolated from a naturally occurring gene or is modified to contain segments of nucleic acids in a manner that would not otherwise exist in nature, or which is synthetic, and which comprises one or more control sequences.

The term "operably linked" refers to a configuration in which a construct sequence is placed at an appropriate position relative to the coding sequence of a polynucleotide such that the control sequence directs, allows or facilitates expression of the coding sequence.

The term "isolated" refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance, etc.). With specific reference to isolated xylanases of the present invention, the isolated xylanase is generally either: a) purified away from other proteins with which it is normally associated; b) when the enzyme is in a concentration not found in nature, or c) when the enzyme is produced in a host cell that is not endogenous.

By "exogeneous" in the context of nucleic acid sequences herein is meant that the exogeneous element is not normally associated with the second element in nature and is thus an artificial or synthetic construct. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the xylanase. In many embodiments, the invention provides nucleic acid constructs that comprise the coding sequence of a xylanase linked to exogeneous construct sequences such as an exogeneous promoter. For clarity, in general the reference to "exogeneous" is in reference to the xylanase and not the host cell. For example, if the host cell is an *A. niger* cell, the promoter that is operably linked to the xylanase gene may be endogenous to *A. niger* but exogeneous to the xylanase. Accordingly, in some embodiments, the invention provides nucleic acid constructs that encode a xylanase enzyme (whether wild type or variant) operably linked to exogeneous construct nucleic acid sequences. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the xylanase.

Suitable construct sequences that can be included in extrachromosomal or integrating expression vectors include, but are not limited to, selectable markers, purificaiton tags, origin(s) of replication and regulatory sequences including but not limited to promoters (inducible and constitutive), enhancers, ribosomal binding sites, start codons, termination codons, Shine-Dalgarno sequences, etc.

By "selection marker" or "selectable marker" or "selection protein" herein is meant a protein that is introduced into a host cell that confers a trait suitable for artificial selection during the growth of the host cells, such that only those cells that contain the selectable marker grow. Thus, a selectable marker is a gene the product of which provides for biocide or viral resistance, resistance to heavy metals, prototrophy to auxotrophs, and the like. Examples of selection markers are outlined below. Accordingly, a "selection gene" is a nucleic acid that encodes a selection protein.

By "extrachromosomal expression vector" (also generally referred to as a "plasmid") herein is meant a self-replicating expression vector (generally a plasmid) that carries genes of interest, which remains within the cell and does not integrate into the genome of the host cell.

By "integrating expression vector" herein is meant a vector that is designed to be inserted into the genome of the host cell, sometimes referred to as "episomes".

III. Xylanases of the Invention

The invention provides thermoactive, thermostable and/or pH stable and active xylanases for use in animal feed application. The invention provides compositions and methods using variant xylanase enzymes comprising at least one amino acid substitution as compared to the wild-type xylanase as set forth in SEQ ID NO:1, as more fully described below.

IV. Variant Xylanases of the Invention

Accordingly, the present invention provides variant xylanases with improved properties that can be used in the animal feed application.

In general, the variant xylanases of the invention have modified, improved biochemical properties as compared to the parental xylanases from *Neocallimastix patriciarum*, or "G1P" (as set forth in SEQ ID NO:1 as shown in FIG. 4A). The biochemical properties of the variant xylanases that can be improved herein include, but are not limited to, one or more of total activity, specific activity, temperature activity, pH activity, total stability, thermostability, pH tolerance, acid stability, formulation stability (in particular pelleting stability), protease stability, performance in the feed pelleting process, performance in animals and/or animal feed and/or protease stability (in particular pepsin stability, found in non-ruminant stomachs), etc.

The variant xylanases of the invention have one or more improved properties as compared to G1P. By "improved" herein is meant a desirable change of at least one biochemical property. "Improved function" can be measured as a percentage increase or decrease of a particular activity, or as a "fold" change, with increases of desirable properties (e.g. total activity, thermoactivity, thermostability and pH tolerance) or decreases of undesirable properties (e.g. protease sensitivity). That is, a variant xylanase may have a 10% increase in total activity or a 10% decrease in protease sensitivity, as compared to G1P. Alternatively, a variant xylanase may have at least 1.1-fold increase in pH tolerance, thermoactivity or protease sensitivity, etc. In general, percentage changes are used to describe changes in biochemical activity of less than 100%, and fold-changes are used to describe changes in biochemical activity of greater than 100% (as compared to the parental enzyme, in many cases, G1P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in FIG. 1D, xylanase variant G2P (colony tracking number: CL00122441) has a more than 1.6 fold increase in total activity at low pH, at least 1.1 fold increase in total activity at pH 5.5, at least 1.1 fold increase in low pH stability, and at least 1.1 fold increase in 90° C. thermostability as compared to G1P. This is calculated by [(activity of variant)/(activity of parent)]. In many embodiments, the improvement is at least one and a tenth fold (1.1 fold), one and a half fold (1.5 fold), 2 fold, 3 fold, 4 fold, 5 fold, 6 fold, 7 fold, 8 fold, 9 fold, or 10 fold or higher.

The variant xylanases of the invention can have an improvement in one or more of a number of biochemical properties, including, but not limited to, total activity, specific activity, temperature activity, pH activity, total stability, temperature stability, pH tolerance, formulation stability (including liquid, solid and pellets), protease stability, performance in the feed pelleting process, performance in animals and/or animal feed and/or protease stability, etc. In some embodiments, improvements are measured as compared to the G1P enzyme. In some embodiments, improvements are measured as compared to the G2P enzyme. In general, improvements are measured as compared to the parental enzyme using the Xylanase Enzymatic Assay, as outlined below.

A. Xylanase Enzymatic Assay to Determine Total Activity

In some embodiments, a Xylanase Enzymatic Assay is employed to determine xylanase total activity, such as the one described in the Examples 3-5. Specifically, plates containing parental xylanase and/or variants of xylanase produced according to Example 2 are thawed. The supernatant is diluted 175-fold into 0.1 M sodium acetate buffer (pH 5.5) for activity assays at pH 5.5. Supernatant is diluted 20-80-fold (depending on the plate) into 0.1 M citrate-phosphate buffer (pH 3.0) for assays to measure pH 3 activity of xylanase, or into a pH 2.5 HCl solution (89 mmol NaCl, 6.6 mmol KCl).

A 1% xylan solution is prepared by dissolving 1.00 g of xylan (corncob, Shanghai Yuanye Bio-Technology Co., Ltd. Supplier #S25540) and 0.320 g sodium hydroxide in 50 mL deionized water, followed by stirring while heated to 100° C. until the xylan is fully dissolved. The xylan substrate is subsequently adjusted to the desired pH. Either pH 5.5 using acetic acid, or pH 3.0 and pH 2.5 with HCl, followed by volume adjustment to 100 mL utilizing 0.1 M sodium acetate buffer (pH 5.5), 0.1 M citrate-phosphate buffer (pH 3.0), or pH 2.5 HCl solution, respectively.

For all assay, low pH and pH 5.5, the respective 1% xylan substrate solution is added to 96-well PCR plates (35 μL/well). The reaction is initiated by addition of 35 μL of the diluted enzyme in either low pH or pH 5.5 buffer, as described in Example 3, to plates containing the same pH 1% xylan solution. The plates are then sealed, incubated at 37° C. shaking at 200 rpm for 2 hours. Following incubation, the reactions are quenched by addition of 80 μL DNS (dinitrosalicylic acid) reagent. The DNS reagent is prepared by addition of 3.15 g 3,5-dinitrosalicylic acid to 500 mL of water while stirring and heating to 45° C. Next, 100 mL of 200 g/L sodium hydroxide solution is slowly added to the stirring solution until fully transparent. Once transparent, 91.0 g potassium sodium tartrate tetrahydrate, 2.50 g phenol, and 2.50 g anhydrous sodium sulfite are added to the stirring solution, followed by 300 mL of water. The solution is cooled to room temperature and the volume adjusted to 1000 mL, filtered and stored for 7 days prior to use in a non-transparent bottle.

The plates after DNS reagent addition are sealed, heated to 95° C. for 5 min using a thermocyder, cooled to 4° C. for 2 min, mixed by inverting 5-6 times, and then centrifuged for 30 s at 1000 rpm. The assay plates are unsealed and 100 μL from each well is transferred to new clear-bottom plates containing 100 μL water and thoroughly mixed. The absorbance of each well is measured at 540 nm and absorbance values indicated enzyme activity in each well. Variant enzyme activity at a specific pH, e.g. low pH (pH 2.5 or 3) or pH 5.5 is compared to the WT (G1P) or G2P enzyme at the same pH to determine activity improvement at the respective pH.

In some embodiments, the parent xylanase enzyme is a polypeptide of SEQ ID NO:1. In some embodiments, the parent xylanase enzyme is a polypeptide of SEQ ID NO:3.

Accordingly, as shown in FIGS. 1 and 2, a number of variant xylanases of the invention exhibit increased total activity at low pH (pH 2.5 or 3), pH 5.5, and/or 90° C.

B. pH Tolerance

In many embodiments, the variant xylanases of the invention have increased pH stability at lower pHs, to address the lower pH of the stomach and gastrointestinal tract of non-ruminant animals. That is, many xylanases have pH profiles that are suboptimal for the lowered pH environment where the activity is desired in the animal. "Increased pH stability" or "increased pH tolerance" in this context means that the variant enzymes are more stable than the parent xylanase (e.g. G1P and/or G2P) under the same pH challenge conditions. That is, the activity of the variant is higher than that of the parental enzyme under identical conditions (generally using the Xylanase Enzymatic assay as shown in Examples 3-5).

Accordingly, in some embodiments the variant xylanases have increased pH stability as compared to a parent xylanase, particularly G1P and/or G2P, for at least 30 minutes at around pH 2.0, at least 30 minutes at around pH 2.5, at least 30 minutes at around pH 3.0, at least 30 minutes at around pH 3.5, at least 30 minutes at around pH 4.0, at least 30 minutes at around pH 4.5, at least 30 minutes at around pH 5.0, at least 30 minutes at around pH 5.5, at least 30 minutes at around pH 6.0, or at least 30 minutes at around pH 6.5.

In some embodiments, the variant xylanases have increased pH stability as compared to a parent xylanase, particularly G1P and/or G2P, for at least 100 minutes at around pH 2.0, at least 100 minutes at around pH 2.5, at least 100 minutes at around pH 3.0, at least 100 minutes at around pH 3.5, at least 100 minutes at around pH 4.0, at least 100 minutes at around pH 4.5, at least 100 minutes at around pH 5.0, at least 100 minutes at around pH 5.5, at least 100 minutes at around pH 6.0, or at least 100 minutes at around pH 6.5.

In some embodiments, the variant xylanases have increased pH stability as compared to a parent xylanase, particularly G1P and/or G2P, for at least 120 minutes at around pH 2.0, at least 120 minutes at around pH 2.5, at least 120 minutes at around pH 3.0, at least 120 minutes at around pH 3.5, at least 120 minutes at around pH 4.0, at least 120 minutes at around pH 4.5, at least 120 minutes at around pH 5.0, at least 120 minutes at around pH 5.5, at least 120 minutes at around pH 6.0, or at least 120 minutes at around pH 6.5.

In some embodiments, the variant xylanases have increased pH stability as compared to a parent xylanase, particularly G1P and/or G2P, for about 120 minutes at around pH 2.0, about 120 minutes at around pH 2.5, about 120 minutes at around pH 3.0, about 120 minutes at around pH 3.5, about 120 minutes at around pH 4.0, about 120 minutes at around pH 4.5, about 120 minutes at around pH 5.0, about 120 minutes at around pH 5.5, about 120 minutes at around pH 6.0, or about 120 minutes at around pH 6.5.

As shown in FIGS. 1 and 2, a number of variant xylanases of the invention exhibited increased tolerance against low pH (pH 2.5 or 3) and/or pH 5.5.

C. Thermostability

In many embodiments, the variant xylanases of the invention have increased thermostability, particularly under the conditions used to produce animal feeds, for example, which frequently use high temperatures during the pelleting process for periods of time that traditionally inactivate many wild type xylanases. "Thermostability" in this context means that the variant enzymes are more stable than the parental xylanase (e.g. G1P or G2P) under the same thermal challenge conditions, that is, the activity of the variant is higher than that of the parental xylanase under identical conditions (generally using the xylanase thermostability assay as outlined herein and as shown in Example 5).

A suitable thermostability assay is as follows. Thawed plates of parental and/or variant xylanase produced according to Example 2 are diluted 4.5-fold into 0.1 M pH 5.5 sodium acetate buffer in a 96-well PCR plate. The remaining enzyme at 4.5-fold diluted is incubated at 90° C. for 15 min or 5 min, followed by chilling to 4° C. for 2 minutes in a thermocyder. The thermo challenged enzymes are diluted 20-fold into 0.1 M pH 5.5 sodium acetate buffer in a new 96-well plate. Diluted enzyme (35 μL) are then added to separate 96-well PCR plates containing 35 μL of 1% xylan substrate (pH 5.5) prepared as described in Example 3. The plates are then sealed, incubated at 37° C. shaking at 200 rpm for 2 hours. Following incubation, the reactions are quenched by addition of 80 μL DNS reagent as described in Example 3. Upon DNS addition the plates are sealed, heated to 95° C. for 5 min, cooled to 4° C. for 2 min, mixed by 5-6 inversions, then centrifuged for 30 s at 1000 rpm. The absorbance of each well is measured at 540 nm indicating enzyme activities. Activity of xylanase variant is compared to the parental enzyme under the same conditions to determine thermostability improvement.

In some embodiments, the variant xylanases are more stable than the parent xylanase when exposed to temperatures of 50° C., 55° C., 60° C., 65° C., 70° C., 75° C., 80° C., 85° C., 90° C. and/or 95° C. for a period of time, generally ranging from about 1, 2, 3, 4, 5, 6, 7, 8, 9 or 10 minutes or longer, depending on the ultimate conditions for the use of the variant xylanase, with some embodiments utilizing thermal challenge times of 5 minutes to 10 minutes, 5 minutes to 15 minutes, 5 minutes to 30 minutes, 10 minutes to 30 minutes, 5 minutes to 60 minutes, 10 minutes to 60 minutes all finding use in the present invention. In one embodiment, a challenge of 70° C., 75° C., 80° C., 85° C., 90° C. or 95° C. is used.

As shown in FIGS. 1 and 2, a number of variant xylanases of the invention exhibited increased tolerance against high temperature (90° C.).

D. Specific Activity Assays

In some embodiments, the variant xylanases of the invention have increased specific activity as compared to a parent xylanase, particularly G1P and/or G2P. By "specific activity" herein is meant the activity per amount (weight) of enzyme, generally determined by dividing the enzymatic activity of a sample by the amount of xylanase enzyme, generally determined as is known in the art.

E. Protease Susceptibility

In some embodiments, the variant xylanases of the invention are less susceptible to protease degradation than the parent enzyme under identical conditions. In some cases, protease degradation during the production of variant xylanases in a production host organism by protease enzymes produced by the host organism can be a problem, thus resulting in lower yield of active enzyme. Similarly, depending on the use of the variant enzymes, there may be other proteases present in the raw substrates or other enzymes for use in combination that can degrade the xylanases.

This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

As needed, as will be appreciated by those in the art, the specific mutations that can be made will depend on the endogenous proteases that the host organism produces, and also generally occurs in surface exposed loop structures or turns that are therefore accessible to proteases.

V. Specific Variant Xylanases

The present invention provides variant xylanase enzymes comprising one or more amino acid substitutions at one or more (e.g., several) positions corresponding to positions 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225 as compared to a parent xylanase enzyme. In some cases, the variant enzyme can comprise 1, 2, 3, 4, 5, 6, 7, 8, 9, 10, 11, 12, 13, 14, 15, 16, 17, 18, 19, 20, 21 or 22 amino acid substitutions at these positions. In some embodiments, the variant exhibits at least 90%, at least 95%, at least 96%, at least 97%, at least 98%, or at least 99%, but less than 100% sequence identity to the parent xylanase enzyme. In some embodiments, the variant xylanase exhibits at least 95%, 96%, 97%, 98% or 99% but less than 100% sequence identity to the parent xylanase enzyme. In one embodiment, the parent xylanase enzyme is SEQ ID NO:1. In another embodiment, the parent xylanase enzyme is SEQ ID NO:3.

In some embodiments, the variant xylanase enzyme comprises at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant enzyme is at least 90% identical to SEQ ID NO:1 and wherein the variant xylanase enzyme has xylanase activity.

In some embodiments, the variant xylanase enzyme comprises at least one amino acid substitution as compared to SEQ ID NO:3, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant enzyme is at least 90% identical to SEQ ID NO:3 and wherein the variant xylanase enzyme has xylanase activity.

In some embodiments, the variant xylanase enzyme comprises at least one amino acid substitution as compared to SEQ ID NO:5, wherein said amino acid substitution is at a position number selected from the group consisting of 1, 2, 5, 6, 8, 12, 15, 18, 20, 23, 25, 26, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant enzyme is at least 90% identical to SEQ ID NO:5 and wherein the variant xylanase enzyme has xylanase activity.

In some embodiments, the variant xylanase enzyme comprises at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant xylanase enzyme has at least 1.1 fold better activity as compared to SEQ ID NO:1 under a condition selected from the group consisting of total activity at about 75° C., total activity at about 80° C., total activity at about 85° C., total activity at about 90° C., and total activity at about 95° C.; and wherein said variant xylanase enzyme is at least 90% identical to SEQ ID NO:1.

In some embodiments, the variant xylanase enzyme comprises at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant xylanase enzyme has at least 1.1 fold better activity as compared to SEQ ID NO:1 under a condition selected from the group consisting of tolerance against pH 2.5, tolerance against pH 3.0, tolerance against pH 3.5, tolerance against pH 4.0, tolerance against pH 4.5, tolerance against pH 5.0, tolerance against pH 5.5, tolerance against pH 6.0, and tolerance against pH 6.5; and wherein said variant xylanase enzyme is at least 90% identical to SEQ ID NO:1. In some embodiments, the variant xylanase enzyme as described herein is at least 95% identical to SEQ ID NO:1.

In some embodiments, the variant xylanase enzyme comprises at least one amino acid substitution as compared to SEQ ID NO:3, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant xylanase enzyme has at least 1.1 fold better activity as compared to SEQ ID NO:3 under a condition selected from the group consisting of total activity at about 75° C., total activity at about 80° C., total activity at about 85° C., total activity at about 90° C., and total activity at about 95° C.; and wherein said variant xylanase enzyme is at least 90% identical to SEQ ID NO:3. In some embodiments, the variant xylanase enzyme as described herein is at least 95% identical to SEQ ID NO:3.

In some embodiments, the variant xylanase enzyme comprises at least one amino acid substitution as compared to SEQ ID NO:3, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant xylanase enzyme has at least 1.1 fold better activity as compared to SEQ ID NO:3 under a condition selected from the group consisting of tolerance against pH 2.5, tolerance against pH 3.0, tolerance against pH 3.5, tolerance against pH 4.0, tolerance against pH 4.5, tolerance against pH 5.0, tolerance against pH 5.5, tolerance against pH 6.0, and tolerance against pH 6.5; and wherein said variant xylanase enzyme is at least 90% identical to SEQ ID NO:3. In some embodiments, the variant xylanase enzyme as described herein is at least 95% identical to SEQ ID NO:3.

In some embodiments, the variant xylanase enzyme comprises at least one amino acid substitution as compared to SEQ ID NO:5, wherein said amino acid substitution is at a position number selected from the group consisting of 1, 2, 5, 6, 8, 12, 15, 18, 20, 23, 25, 26, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant xylanase enzyme has at least 1.1 fold better activity as compared to SEQ ID NO:5 under a condition selected from the group consisting of total activity at about 75° C., total activity at about 80° C., total activity at about 85° C., total activity at about 90° C., and total activity at about 95° C.; and wherein said variant xylanase enzyme is at least 90% identical to SEQ ID NO:5. In some embodiments, the variant xylanase enzyme as described herein is at least 95% identical to SEQ ID NO:5.

In some embodiments, the variant xylanase enzyme comprises at least one amino acid substitution as compared to SEQ ID NO:5, wherein said amino acid substitution is at a position number selected from the group consisting of 1, 2, 5, 6, 8, 12, 15, 18, 20, 23, 25, 26, 28, 35, 38, 51, 52, 54, 56, 86, 89, 90, 93, 99, 105, 119, 120, 121, 133, 135, 149, 160, 168, 178, 185, 190, 194, 201, 224, and 225, wherein said variant xylanase enzyme has at least 1.1 fold better activity as compared to SEQ ID NO:5 under a condition selected from the group consisting of tolerance against pH 2.5, tolerance against pH 3.0, tolerance against pH 3.5, tolerance against pH 4.0, tolerance against pH 4.5, tolerance against pH 5.0, tolerance against pH 5.5, tolerance against pH 6.0, and tolerance against pH 6.5; and wherein said variant xylanase enzyme is at least 90% identical to SEQ ID NO:5. In some embodiments, the variant xylanase enzyme as described herein is at least 95% identical to SEQ ID NO:5.

In some embodiments, the variant xylanase enzyme comprises at least one amino acid substitution as compared to a parent xylanase enzyme, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, or fifteen of said positions. In one embodiment, the parent xylanase enzyme is SEQ ID NO:1. In another embodiment, the parent xylanase enzyme is SEQ ID NO:3. In a further embodiment, the parent xylanase enzyme is SEQ ID NO:5.

In some embodiments, the variant xylanase enzyme comprises at least one amino acid substitution as compared to SEQ ID NO:1, wherein said amino acid substitution is selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V27I, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, H131F, H131P, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In some embodiments, the variant xylanase enzyme comprises at least one amino acid substitution as compared to SEQ ID NO:1, wherein said amino acid substitution(s) is selected from the group consisting of S5I, T51C, K15T, G25E, S5K, T51E, K20C, T51R, Q1P, T51Q, S8C, K20V, Q12T, G26C, S8H, K20S, K15R, Q12L, S6K, Q1H, S8R, K15H, S5R, G26T, G26N, K15V, S6T, S6H, G26R, V27W, T149R, G224K, D225Y, N160Q, T190P, G224L, G224M, G224T, Q168S, N160K, T190H, N160R, S105D, G56R, S90I, F120Y, N54D, S89C, F120H, G56T, S90C, S105H, V99A, G56H, S89V, S133L, S90E, V99G, S133T, S90A, S90F, S133K, N54G, S89A, G93L, F120D, S89T, S105I, S105N, H131F, P121G, F120S, H131P, G56K/P119Q, G56K/F120Y/S133D, G56K/S178T, T51S/S133D, V27I/ G56K/N160K, P121R/S133D/N160K, G18S/V27I/G56K/ N160K/L194M, G18S/N160K, G18S/G28D, G56K/P119Q/ P121R/S133D/L194M, G18S/G56K/F120Y, V27I/N160K, T51S/P119Q/S133D/N160K/S178T, G18S/T23S/G56K/ P119Q/F120Y/P121R/S133D, T51S/F120Y, G56K/S133D/ N160K, T51S/G56K/F120Y/S178T, G56K/N160K, T51S/ G56K/S133D/N160K, T51S/P119Q/F120Y/N160K, Q1P/ S8R/K20V/T51C/S89C/S90H, Q1P/S8H/K20V, Q1P/ K15T/K20C/V27W/V99A, S8C/K20V/V27W/H131F, S8H/ H131F, V27W/H131F, Q1P/K20C/V27W, K15T/K20V/ V27W, K20C/V27W/S89V/S90H, Q1P/S8H/K15T/V27W/ H131F, Q1P/S8C/K15T/K20V/V27W/S89T/H131F, Q1P/ S8H/K15H/V27W/H131F, Q1P/S8H/V27W/S89T, Q1P/ S8R/S89A/S90H/H131F, K20V/V27W/T51C/S89C/S90H/ H131F, Q1P/H131F, K15H/K20V/V27W/H131F/G224K, Q1P/S8R/K15T/K20V/V27W/S89A/S90H/V99A/H131F/ G224L, Q1P/S8H/T51C/H131F, Q1P/K20V/V27W/V99A/ H131F, Q1P/S8R/K20V/V27W/T51C/G224L, Q1P/S8R/ K15T/K20C/V27W/S89A/H131F, K15T/K20V/V27W/ H131F, Q1P/S8R/K20C/V27W, S8H/K20V/V27W, Q1P/ S8H/K15H/K20V/V27W/S89C/S90H/V99A/H131F, Q1P/ S8R/K15H/V27W/V99A, K15H/V27W, S90E/H131F, Q1P/ K15H/K20V/V27W/T51C/S90H/H131F, K15T/K20C/ V27W/H131F, V27W/G224L, K20V/V27W/H131F, K15T/ K20V/V27W/T51C/G224L, Q1P/S9C/H131F, Q1P/S8R/ K15H/K20V/V27W/T51C/S90E, Q1P/S8R/V27W, Q1P/ S8C/V27W/T51C/H131F, Q1P/S8H, K15T/K20C/V27W/ S90H/H131F, K15T/V27W/S90H, Q1P/K20V/H131F, K15T/V27W, Q1P/H131F/G224L, S8C/K15T/K20V/ V27W/T51C/S90H, Q1P/K15T/K20C/V27W/T51C/S89C/ S90H/H131F, Q1P/S8H/K20C/V27W, Q1P/S90H/N160K/ T190H, Q1P/S5K/G26N/V27W/F120Y/Q168S/T190H, Q12T/K20C/G26T/S89C/H131F/Q168S, S5I/K20S/S89T/ V99A/F120D/H131F/Q168S/T190H, Q1P/S5K/K20S/ S89C/F120Y, S6H/G56K/V99A/Q168S/T190H, S8R/ K20V/T190H, K15T/G26T/G56K/H131F/N160K/T190H, S8H/K20C/S105N/H131F/N160Q/Q168S, Q1H/S5R/ K15V/G56K/Q168S, K20S/G56K/F120Y/N160Q/T190H, S8R/H131F/T190H, G26N/V27W/G56K/S90H/H131F/ Q168S/T190H, S89V/H131F/Q168S, S5R/Q12L/K15T/ G26N/V27W/G56K/F120Y/H131F, S6H/S8R/K20S/S89A/ V99A, Q1P/S5R/G26T/S90C/H131F/Q168S/T190H, S8H/

K20C/T51R/S89A/P121R/N160K/T190H, Q1P/S5R/Q12T/ K15V/G26T/V27W/S90E/H131F/G224K, Q1P/S5R/K20S/ G56K/S89C/H131F/N160K/Q168S/T190H, Q1H/S5K/ Q12L/S90H/S105N/T190H, S8C/K20C/T51C/S89A/ Q168S, G26N/V27W/S105N/Q168S/G224L, S5I/S90H/ S105N/F120Y/P121R/H131F/Q168S/G224K, S6H/S8C/ K20S/T51S/F120Y/P121R/T190H, S5K/V99G/T190H, S5K/K20V/G56K/H131F/Q168S, S8R/T51R/S89H/H131F/ T190H, Q1P/S5R/S8R/V99A/N160Q, S8R/T51C/F120D/ Q168S/G224L, Q1P/V27W, Q1P/Q12T/K20V/G56K/ S105N/N160Q/T190H/G224K, Q1H/S5I/Q12L/K15R/ H131F, S89C/F120D/H131F/N160Q/G224L, K20C/P121R, K20S/V27W/T51Q/S105N/F120D/P121R/N160Q/T190H/ G224M, Q1H/S8C/K20V/G56K/S89A/H131F/T190H/ G224L, S8H/G26T, S6H/S8C/K20S/S89C/T190H, K20S/ T51C/S89V/T190H, Q1H/Q12L/K15R/V27W/G56K/ V99A/N160K/T190H, S8C/K19R/S105N/H131F/T190H, Q1H/S5R/Q12L/K20C/G56K/H131F/T190H, Q1H/S5I/ Q12T/K15V/G26T/G56K/S90E/S105N/Q168S, S6H/ K20C/S89T, Q1H/S5R/K15R/G26N/G56K/H131F/T190H/ G224K, S89V/V99G/T190H, Q1H/S5I/Q12L/K15T/ Q168S, Q12L/K15R/S90H/H131F/Q168S/T190H, Q1H/ S5I/T190H, Q1P/S8H/K20V/T51Q/S89T/V99A/F120D/ T190H, S8R/K20S/G56K/K86T/S89A/V99A/H131F, S8C/ Q12T/K15V/G56K/T190H, K20S/S89C/F120Y/H131F/ T190H, Q1P/K20V/G56K/S90E/S105N/H131F, S5I/K20S/ G26N/V27W/G56K/S90H/S105N/Q168A/T190H, Q1P/ S2K/S6H/S8R/S105N/Q168S/G224K, S8H/K20C/T51R/ S89A/N160K/Q168S, Q1H/S5R/Q12T/K15R/G26N/S89A/ V99G/F120D/P121R/T190H/G224M, S8C/K20S/G56K/S89C/V99G/F120D/P121R/T190H, S6H/S8H/K20C/T51R/S89A/P121R/T190H, Q1P/S5K/T51Q/V99G, Q1P/S5I/S89V/S105N/H131F/Q168S, S8H/K15V/K20C/T51Q/S89A/S105N/Q168S, Q1P/S5I/K15R/G26T/S89C/V99G/F120Y/N160Q/T190H/G224K, S89C/H131F/Q168S/T190H, Q1P/S5K/Q12L/K20C/T51Q/S89V/F120Y/N160K/Q168S/T190H, Q1H/S5K/G56K/F120D/P121R/Q168S, T51E/V99A/P121R/H131F/N160Q/Q168S/T190H/G224K, Q1P/S5R/Q12T/K15H/G26N/V27W/G56K/S90C/S105N/T190H, S6H/S8R/K20C/T51C/F120D/T190H, S8R/K20S/F120D/P121R, S5R/S105N/Q168S/T190H, Q1H/S5R/K15V/G26N/V27W/H131F/Q168S/T190H, Q1H/S5R/Q12L/K15T/S90E/S105N/H131F/Q168S, K20V/S89V/V99A/N160K/Q168S/G224K, S90C/S105N/H131F, S6H/S8H/K20V/T190H, S8H/T51E/V99G/Q168S/T190H, S5R/Q12L/K20V/S89C/Q168S/T190H, Q1P/S5K/Q12T/K15H/G26N/V27W/G56K/S89C/H131F, K15R/G56K/T190H, Q1H/S5K/Q12T/K15T/G26T/G56K/S89C/H131F/N160K/Q168S, S6H/S8R/K20V/T51E/S90H/S105N/H131F/T135S/Q168S/T190H, Q1P/S5K/Q12L/K15R/G56K/S89T/F120D, Q12L/H131F/N160K/T190H, Q1H/S5K/Q12T/K15H/G26N/V27W/G56K/H131F, Q1P/S5K/Q12T/G56K/S105N/H131F/Q168S/T190H/G224L, V27W/S90C/V99G/S105N/F120Y/N160K/Q168S, G56K/S90C/H131F/Q168S/T190H, Q1P/S5R/G26T/G56K/S105N/H131F/Q168S/T190H, S8C/T51E/S89A/V99A/H131F/Q168S/T190H, S5K/K15H/G26T/S90H/H131F, G26N/G56K/S89T/H131F/Q168S/T190H/G224K, Q1P/Q12L/K15T/G26N/V27W/S90H/S105N/H131F/T190H, G56K/S90C, K20S/S89V/V99G/S105N/T190H, S5I/G26N/G56K/V99G/S105N, Q1P/S5R/G56K/H131F/N160K/T190H, Q1H/S5I/K20V/S89C, K20C/T51Q/S89C/V99G/F120D/P121R/T190H, S8R/Q12T/K15V/T51E/S89A/V99A/F120D/P121R/T190H, G26N/V27W/S105N/H131F/Q168S, S6H/S89T/V99A/F120D/P121R/N160Q/Q168S/T190H, T51Q/H131F, Q1P/S5R/Q12L/K15V/V27W/G56K/V99A/S105N/F120D/N160Q/Q168S, Q1P/S5R/G26N/G56K/S90H/S105N/F120D/P121R/T190H, S5R/Q12T/K20V/G56K/F120Y, S105N/F120D/P121R/T190H, S8R/K20C/G26N/V27W/G56K/H131F/T190H, Q1H/V27W/G56K/S90C, G56K/S90C/H131F/Q168S/T190H, Q12L/K15R/V27W/G56K/S90E, Q1H/S105N/T190H, G56K/S89T/S105N/P121R/H131F/Q168S/G224K, K20S/S89A/V99G/S105N/N160Q/T190H, Q1P/P121R/H131F/N160Q/T190H, K15V/T51Q/S89V/H131F/G224K, Q1P/K20S/N160K/T190H, S8H/G56K/S89V/F120Y/P121R/N160Q/Q168S/T190H, Q1H/S5K/V27W/G56K/Q168S/T190H, F120D/P121R/Q168S, S8H/K20V/T51S/V99A/T190H, S9R/T51E/S89T/V99G/N160K/T190H, K20S/S89C/T190H, K20S/S90E/G224M, K15V/G56K/S89T/T190H, S6H/S8R/Q12L/K15V/G26T/V27W/G56K/Q168S, Q1P/S5I/K20S/G56K/S90E/H131F/Q168S, S6H/F120Y/T190H, S8H/K20V/T51S, S105N/H131F, S5I/Q12T/K15H/G26T/V27W/G56K/S90H/S105N/H131F/N160K/T190H, Q1H/S5R/G26T/G56K/S105N/H131F/G224K, S5I/S89C/S105N/H131F/Q168S, Q1P/S5R/Q12L/K15R/G56K/S90H/F120D/P121R/H131F/N160K, S105N/H131F/Q168S, S6H/S8R/K20V/G56K/F120D/P121R/H131F/T190H, Q1P/S5I/G26N/V27W/S90E/H131F/Q168S/G224M, G56K/T190H, S8R/K20C/T51E/S89V/Q168S/G224M, S8C/K20S/S89A/F120Y/P121R/N160Q, S5R/S89T/F120Y/P121R/T190H, G26N/V27W/G56K/S105N/H131F/Q168S, S6H/S8R/S89A/F120Y, Q1P/S5R/Q12L/K15R/G26T/S90H/Q168S/T190H, K20C/H131F, K20C/V27W/H131F, K15H/K20C/H131F, K15H/K20V/V27W/S89A/H131F, K15H/S89C/H131F, K15H/V27W/H131F, K15R/K20C/H131F, K15R/K20C/S89A/H131F, K15R/K20C/S89C/H131F, K15R/K20C/S89V/H131F, K15R/K20V/H131F, K15R/S89A/H131F, K15R/S89C/H131F, K15R/S89V/H131F, K20C/H131F, K20C/S89T/H131F, K20C/V27W/S89T/H131F/E185K, K20V/H131F, K20V/S89C/H131F, K20V/S89T/H131F, K20V/S89V/H131F, S89A/H131F, S89C/H131F, S8C/K15H/K20C/S89T/H131F, S8C/K20C/H131F, S8C/K20V/S89C/H131F, S8C/K20V/S89T/H131F, S8H/K15R/K20C/S89T/H131F, S8H/K20C/S89T/H131F, S8H/K20C/V27W/H131F, S8H/K20V/H131F, S8H/K20V/S89C/H131F, S8H/K20V/V27W/S89T/H131F, S8R/K15H/K20V/S89C/H131F, S8R/K15R/K20C/H131F, S8R/K20C/S89C/H131F, V27W/S89C/H131F, V27W/S89T/H131F, G26T/V27W/H131F, V27W/S89A/H131F, V27W/H131F/S133T, G26T/V27W/S89A/H131F, G26T/V27W/H131F/S133T, V27W/S89A/H131F/S133T, G26T/V27W/S89A/H131FS/S133T, G26T/V27W/S35R/S89A/H131FS/S133R, and V27W/N38Y/F52W/G56Y/H131F/G201L.

In some embodiments, the variant xylanase enzyme comprises at least one amino acid substitution as compared to SEQ ID NO:1, wherein said amino acid substitution is H131F.

In some embodiments, the variant xylanase enzyme comprises at least one amino acid substitution as compared to SEQ ID NO:1, wherein said amino acid substitutions are V27W/H131F.

In some embodiments, the invention provides a variant xylanase enzyme as described herein, wherein said variant xylanase enzyme comprises an amino acid substitution H131F, and further comprises at least one amino acid substitution selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V27I, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In some embodiments, the invention provides a variant xylanase enzyme as described herein, wherein said variant xylanase enzyme comprises amino acid substitutions V27W/H131F, and further comprises at least one amino acid substitution selected from the group consisting of Q1H, Q1P, S2K, S5I, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

In some embodiments, the variant xylanase enzymes comprise one or more variants selected from FIGS. 1 and 2.

In some embodiments, the variant xylanase enzyme is an isolated variant xylanase enzyme.

In some embodiments, the variant xylanase comprises an amino acid substitution of the Glutamine at position 1 as compared to the wild type xylanase (SEQ ID NO:1) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is Q1H. In some embodiments, the amino acid substitution is Q1P.

In some embodiments, the variant xylanase comprises an amino acid substitution of the Serine at position 2 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S2K.

In some embodiments, the variant xylanase comprises an amino acid substitution of the Serine at position 5 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S5I. In some embodiments, the amino acid substitution is S5K. In some embodiments, the amino acid substitution is S5R.

In some embodiments, the variant xylanase comprises an amino acid substitution of the Serine at position 6 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S6H. In some embodiments, the amino acid substitution is S6K. In some embodiments, the amino acid substitution is S6T.

In some embodiments, the variant xylanase comprises an amino acid substitution of the Serine at position 8 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing proline (due to steric effects). In some embodiments, the amino acid substitution is S8C. In some embodiments, the amino acid substitution is S8H. In some embodiments, the amino acid substitution is S8R.

In some embodiments, the variant xylanase comprises an amino acid substitution of the Glutamine at position 12 as compared to the wild type xylanase (SEQ ID NO:1) mature protein. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q12L. In some embodiments, the amino acid substitution is Q12T.

In some embodiments, the variant xylanase comprises an amino acid substitution of the Lysine at position 15 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is K15H. In some embodiments, the amino acid substitution is K15R. In some embodiments, the amino acid substitution is K15T. In some embodiments, the amino acid substitution is K15V.

In some embodiments, the variant xylanase comprises an amino acid substitution of the Glycine at position 18 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G18S.

In some embodiments, the variant xylanase comprises an amino acid substitution of the Lysine at position 20 as compared to the wild type xylanase (SEQ ID NO:1) mature protein. In some embodiments, the substitution is with any other of the 19 naturally occurring amino acids, namely glycine, serine, threonine, asparagine, glutamic acid, glutamine, aspartic acid, arginine, histidine, cysteine, alanine, isoleucine, leucine, methionine, proline, phenylalanine, tryptophan, valine and tyrosine, with some embodiments not utilizing proline (due to steric effects). In some embodiments, the amino acid substitution is K20C. In some embodiments, the amino acid substitution is K20S. In some embodiments, the amino acid substitution is K20V.

In some embodiments, the variant xylanase comprises an amino acid substitution of the Threonine at position 23 as compared to the wild type xylanase (SEQ ID NO:1) mature protein. In some embodiments, the substitution is with any other of the 19 naturally occurring amino acids, namely glycine, serine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T23S.

In some embodiments, the variant xylanase comprises an amino acid substitution of the Glycine at position 25 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G25E.

In some embodiments, the variant xylanase comprises an amino acid substitution of the Glycine at position 26 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G26C. In some embodiments, the amino acid substitution is G26N. In some embodiments, the amino acid substitution is G65R. In some embodiments, the amino acid substitution is G26T.

In some embodiments, the variant xylanase comprises an amino acid substitution of the Valine at position 27 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine, with some embodiments not utilizing cysteine (due to possible disulfide formation) or proline (due to steric effects). In some embodiments, the amino acid substitution is V27I. In some embodiments, the amino acid substitution is V27W.

In some embodiments, the variant xylanase comprises an amino acid substitution of the Glycine at position 28 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G28D.

In some embodiments, the variant xylanase comprises an amino acid substitution of the Serine at position 35 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S35R.

In some embodiments, the variant xylanase comprises an amino acid substitution of the Asparagine at position 38 as compared to the wild type xylanase (SEQ ID NO:1) mature protein. In some embodiments, the substitution is with any other of the 19 naturally occurring amino acids, namely, serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N38Y.

In some embodiments, the variant xylanase comprises an amino acid substitution of the Threonine at position 51 as compared to the wild type xylanase (SEQ ID NO:1) mature protein. In some embodiments, the substitution is with any other of the 19 naturally occurring amino acids, namely, asparagine, serine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing proline (due to steric effects). In some embodiments, the amino acid substitution is T51C. In some embodiments, the amino acid substitution is T51E. In some embodiments, the amino acid substitution is T51Q. In some embodiments, the amino acid substitution is T51R. In some embodiments, the amino acid substitution is T51S.

In some embodiments, the variant xylanase comprises an amino acid substitution of the Phenylalanine at position 52 as compared to the wild type xylanase (SEQ ID NO:1) mature protein. In some embodiments, the substitution is with any other of the 19 naturally occurring amino acids, namely, asparagine, serine, threonine, glutamic acid, glutamine, aspartic acid, lysine, arginine, histidine, cysteine, glycine, alanine, isoleucine, leucine, methionine, proline, tryptophan, valine and tyrosine, with some embodiments not utilizing cysteine (due to possible disulfide formation) or proline (due to steric effects). In some embodiments, the amino acid substitution is F52W.

In some embodiments, the variant xylanase comprises an amino acid substitution of the Asparagine at position 54 as compared to the wild type xylanase (SEQ ID NO:1) mature protein. In some embodiments, the substitution is with any other of the 19 naturally occurring amino acids, namely, phenylalanine, serine, threonine, glutamic acid, glutamine, aspartic acid, lysine, arginine, histidine, cysteine, glycine, alanine, isoleucine, leucine, methionine, proline, tryptophan, valine and tyrosine, with some embodiments not utilizing cysteine (due to possible disulfide formation) or proline (due to steric effects). In some embodiments, the amino acid substitution is N54D. In some embodiments, the amino acid substitution is N54G.

In some embodiments, the variant xylanase comprises an amino acid substitution of the Glycine at position 56 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G56H. In some embodiments, the amino acid substitution is G56K. In some embodiments, the amino acid substitution is G56R. In some embodiments, the amino acid substitution is G56T. In some embodiments, the amino acid substitution is G56Y.

In some embodiments, the variant xylanase comprises an amino acid substitution of the lysine at position 86 as compared to the wild type xylanase (SEQ ID NO:1) mature protein. In some embodiments, the substitution is with any other of the 19 naturally occurring amino acids, namely, asparagine, phenylalanine, serine, threonine, glutamic acid, glutamine, aspartic acid, arginine, histidine, cysteine, glycine, alanine, isoleucine, leucine, methionine, proline, tryptophan, valine and tyrosine, with some embodiments not utilizing cysteine (due to possible disulfide formation) or proline (due to steric effects). In some embodiments, the amino acid substitution is K86T.

In some embodiments, the variant xylanase comprises an amino acid substitution of the Serine at position 89 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing proline (due to steric effects). In some embodiments, the amino acid substitution is S89A. In some embodiments, the amino acid substitution is S89C. In some embodiments, the amino acid substitution is S89T. In some embodiments, the amino acid substitution is S89V.

In some embodiments, the variant xylanase comprises an amino acid substitution of the Serine at position 90 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing proline (due to steric effects). In some embodiments, the amino acid substitution is S90A. In some embodiments, the amino acid substitution is S90C. In some embodiments, the amino acid substitution is S90E. In some embodiments, the amino acid substitution is S90F. In some embodiments, the amino acid substitution is S90I. In some embodiments, the amino acid substitution is S90H.

In some embodiments, the variant xylanase comprises an amino acid substitution of the Glycine at position 93 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G93L.

In some embodiments, the variant xylanase comprises an amino acid substitution of the Valine at position 99 as compared to the wild type xylanase (SEQ ID NO:1) mature protein. In some embodiments, the substitution is with any other of the 19 naturally occurring amino acids, namely glycine, serine, threonine, asparagine, glutamic acid, glutamine, aspartic acid, lysine, arginine, histidine, cysteine, alanine, isoleucine, leucine, methionine, proline, phenylalanine, tryptophan, and tyrosine, with some embodiments not utilizing cysteine (due to possible disulfide formation) or proline (due to steric effects). In some embodiments, the amino acid substitution is V99A. In some embodiments, the amino acid substitution is V99G.

In some embodiments, the variant xylanase comprises an amino acid substitution of the Serine at position 105 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S105D. In some embodiments, the amino acid substitution is S105H. In some embodiments, the amino acid substitution is S105I. In some embodiments, the amino acid substitution is S105N.

In some embodiments, the variant xylanase comprises an amino acid substitution of the Proline at position 119 as compared to the wild type xylanase (SEQ ID NO:1) mature protein. In some embodiments, the substitution is with any other of the 19 naturally occurring amino acids, namely, serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P119Q.

In some embodiments, the variant xylanase comprises an amino acid substitution of the Phenylalanine at position 120 as compared to the wild type xylanase (SEQ ID NO:1) mature protein. In some embodiments, the substitution is with any other of the 19 naturally occurring amino acids, namely, serine, threonine, asparagine, glutamic acid, glutamine, aspartic acid, lysine, arginine, histidine, cysteine, glycine, alanine, isoleucine, leucine, methionine, proline, tryptophan, valine and tyrosine, with some embodiments not utilizing cysteine (due to possible disulfide formation) or proline (due to steric effects). In some embodiments, the amino acid substitution is F120D. In some embodiments, the amino acid substitution is F120H. In some embodiments, the amino acid substitution is F120S. In some embodiments, the amino acid substitution is F120Y.

In some embodiments, the variant xylanase comprises an amino acid substitution of the Proline at position 121 as compared to the wild type xylanase (SEQ ID NO:1) mature protein. In some embodiments, the substitution is with any other of the 19 naturally occurring amino acids, namely, serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P121G. In some embodiments, the amino acid substitution is P121R.

In some embodiments, the variant xylanase comprises an amino acid substitution of the histidine at position 131 as compared to the wild type xylanase (SEQ ID NO:1) mature protein. In some embodiments, the substitution is with any other of the 19 naturally occurring amino acids, namely, proline, serine, threonine, asparagine, glutamic acid, glutamine, aspartic acid, lysine, arginine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is H131F. In some embodiments, the amino acid substitution is H131P.

In some embodiments, the variant xylanase comprises an amino acid substitution of the Serine at position 133 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S133D. In some embodiments, the amino acid substitution is S133K. In some embodiments, the amino acid substitution is S133L. In some embodiments, the amino acid substitution is S133T. In some embodiments, the amino acid substitution is S133R.

In some embodiments, the variant xylanase comprises an amino acid substitution of the Threonine at position 135 as compared to the wild type xylanase (SEQ ID NO:1) mature protein. In some embodiments, the substitution is with any other of the 19 naturally occurring amino acids, namely, serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T135S.

In some embodiments, the variant xylanase comprises an amino acid substitution of the Threonine at position 149 as compared to the wild type xylanase (SEQ ID NO:1) mature protein. In some embodiments, the substitution is with any other of the 19 naturally occurring amino acids, namely, serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is T149R.

In some embodiments, the variant xylanase comprises an amino acid substitution of the Asparagine at position 160 as compared to the wild type xylanase (SEQ ID NO:1) mature protein. In some embodiments, the substitution is with any other of the 19 naturally occurring amino acids, namely, threonine, serine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N160K. In some embodiments, the amino acid substitution is N160Q. In some embodiments, the amino acid substitution is N160R.

In some embodiments, the variant xylanase comprises an amino acid substitution of the Glutamine at position 168 as compared to the wild type xylanase (SEQ ID NO:1) mature protein. In some embodiments, the substitution is with any other of the 19 naturally occurring amino acids, namely, asparagine, threonine, serine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is Q168S. In some embodiments, the amino acid substitution is Q168A.

In some embodiments, the variant xylanase comprises an amino acid substitution of the Serine at position 178 as compared to the wild type xylanase (SEQ ID NO:1) mature protein. In some embodiments, the substitution is with any other of the 19 naturally occurring amino acids, namely, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S178T.

In some embodiments, the variant xylanase comprises an amino acid substitution of the Glutamic acid at position 185 as compared to the wild type xylanase (SEQ ID NO:1) mature protein. In some embodiments, the substitution is with any other of the 19 naturally occurring amino acids, namely, serine, threonine, asparagine, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is E185K.

In some embodiments, the variant xylanase comprises an amino acid substitution of the Threonine at position 190 as compared to the wild type xylanase (SEQ ID NO:1) mature protein. In some embodiments, the substitution is with any other of the 19 naturally occurring amino acids, namely, glutamic acid, serine, asparagine, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is T190H. In some embodiments, the amino acid substitution is T190P.

In some embodiments, the variant xylanase comprises an amino acid substitution of the Leucine at position 194 as compared to the wild type xylanase (SEQ ID NO:1) mature protein. In some embodiments, the substitution is with any other of the 19 naturally occurring amino acids, namely, glutamic acid, serine, threonine, asparagine, glutamine, aspartic acid, lysine, arginine, histidine, cysteine, glycine, alanine, isoleucine, methionine, proline, phenylalanine, tryptophan, valine and tyrosine, with some embodiments not utilizing cysteine (due to possible disulfide formation) or proline (due to steric effects). In some embodiments, the amino acid substitution is L194M.

In some embodiments, the variant xylanase comprises an amino acid substitution of the Glycine at position 201 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G201L.

In some embodiments, the variant xylanase comprises an amino acid substitution of the Glycine at position 224 as compared to the wild type xylanase (SEQ ID NO:1) mature protein. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G224K. In some embodiments, the amino acid substitution is G224L. In some embodiments, the amino acid substitution is G224M. In some embodiments, the amino acid substitution is G224T.

In some embodiments, the variant xylanase comprises an amino acid substitution of the Aspartic acid at position 225 as compared to the wild type xylanase (SEQ ID NO:1) mature protein. In some embodiments, the substitution is with any other of the 19 naturally occurring amino acids, namely glycine, serine, threonine, asparagine, glutamic acid, glutamine, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is D225Y.

In some embodiments, the variant xylanase enzymes of the invention have at least 90%, 95%, 96%, 97%, 98% or 99% sequence identity to SEQ ID NO:1, SEQ ID NO:3, or SEQ ID NO:5. In some embodiments, the variant xylanase enzyme is SEQ ID NO:3. In some embodiments, the variant enzyme is SEQ ID NO:5.

The amino acid changes that may be present in addition to the specific substitutions described herein may be of a minor nature, that is conservative amino acid substitutions or insertions that do not significantly affect the folding and/or activity of the protein; small deletions, typically of 1 to about 30 amino acids; small amino- or carboxyl-terminal extensions, such as an amino-terminal methionine residue; a small linker peptide of up to about 20 to about 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly.

In some embodiments, the invention relates to xylanase variants having improved thermal properties, such as thermostability, heat-stability, pH stability, steam stability, acid stability and activity, and/or pelleting stability, with variant enzymes having high tolerance to high temperature and high tolerance to low pH of particular use in many embodiments.

In some embodiments, the invention relates xylanase variants having improved pelleting stability and/or improved acid-stability.

The compositions and methods of the invention thus relates to xylanase variants having an improved pH tolerance profile.

The compositions and methods of the invention thus relates to xylanase variants having improved protease stability, in particular pepsin stability, found in non-ruminant stomachs.

The compositions and methods of the invention thus relates to xylanase variants having improved performance in animal feed (such as an improved release and/or degradation of xylanase).

VI. Nucleic Acids of the Invention

The present invention additionally provides nucleic acids encoding the variant xylanases of the invention. As will be appreciated by those in the art, due to the degeneracy of the genetic code, an extremely large number of nucleic acids may be made, all of which encode the variant xylanases of the present invention. Thus, having identified a particular amino acid sequence, those skilled in the art could make any number of different nucleic acids, by simply modifying the sequence of one or more codons in a way which does not change the amino acid sequence of the protein. Thus, providing the amino acid sequence allows the generation of a very large number of different nucleic acid sequences encoding the proteins.

In some embodiments, specific variant xylanases are encoded by specific nucleic acid sequences, as are listed in FIG. 4.

As is known in the art, the nucleic acids encoding the components of the invention can be incorporated into expression vectors as is known in the art, and depending on the host cells used to produce the heterodimeric antibodies of the invention. Generally, the nucleic acids are operably linked to any number of regulatory elements (promoters, origin of replication, selectable markers, ribosomal binding sites, inducers, etc.). The expression vectors can be extrachromosomal or integrating vectors.

The nucleic acids and/or expression vectors of the invention are then transformed into any number of different types of host cells as is well known in the art, including mammalian, bacterial, yeast, insect and/or fungal cells, with bacteria and fungi finding use in many embodiments.

In some embodiments, the present invention provides a nucleic acid encoding the variant xylanase enzyme as described herein.

In some embodiments, the present invention provides a nucleic acid encoding the variant xylanase enzyme as described herein, wherein the nucleic acid is codon optimized for a host organism for expression of the variant xylanase enzyme in said organism.

In some embodiments, the present invention provides the nucleic acid as described herein, wherein the nucleic acid comprises a sequence that has at least 80% sequence identity to the sequence of SEQ ID NO:4 or SEQ ID NO:6.

In some embodiments, the present invention provides the nucleic acid as described herein, wherein the nucleic acid comprises the sequence of SEQ ID NO:4 or SEQ ID NO:6.

A. Preparation of Variants

The nucleic acids encoding the variant xylanases of the invention can be prepared using any mutagenesis procedure known in the art, such as site-directed mutagenesis and synthetic gene construction as are well known in the art.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips. A preferred technique is GenScript®.

i. Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* phytase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators for filamentous fungal host cells are obtained from the genes for *Aspergillus nidulans* anthranilate synthase, *Aspergillus niger* phytase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* phytase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant xylanase being expressed into the cell's secretory pathway. The 5'-end of the coding sequence of the polynucleotide may inherently contain a signal peptide coding sequence naturally linked in translation reading frame with the segment of the coding sequence that encodes the variant xylanase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant xylanase. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* phytase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In some embodiments, the yeast is *Saccharomyces cerevisiae*. In filamentous fungi, for example, the *Aspergillus niger* xylanase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynudeotide encoding the variant would be operably linked with the regulatory sequence.

1. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynudeotide may be expressed by inserting the polynudeotide or a nucleic acid construct comprising the polynudeotide into an appropriate vector for expression. In creating the expression vector, the coding sequence is located in the vector so that the coding sequence is operably linked with the appropriate control sequences for expression.

In some embodiments, the present invention provides an expression vector comprising the nucleic acid as described herein.

The recombinant expression vector may be any vector (e.g., a plasmid or virus) that can be conveniently subjected to recombinant DNA procedures and can bring about expression of the polynudeotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynudeotide of the present invention can be inserted into a host cell to increase production of a variant. An increase in the copy number of a polynucleotide can be obtained by integrating at least one additional copy of the sequence into the host cell genome or by including an amplifiable selectable marker gene with the polynudeotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

2. Codon Optimization

Codon optimization can be employed with any of the variant xylanase polypeptides of the present invention, in order to optimize expression in the host cell employed. Such methods are well known in the art and described in, for example, WO 2007/142954. In heterologous expression systems, optimization steps can improve the ability of the host to produce the desired variant xylanase polypeptides. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases. The following paragraphs discuss potential problems that may result in reduced heterologous protein expression, and techniques that may overcome these problems.

In some embodiments, reduced heterologous protein expression results from a rare codon-induced translational pause. A rare codon-induced translational pause includes the presence of codons in the polynucleotide of interest that are rarely used in the host organism can have a negative effect on protein translation due to their scarcity in the available tRNA pool. One method of improving optimal translation in the host organism includes performing includes performing codon optimization which can result in rare host codons being modified in the synthetic polynucleotide sequence.

In some embodiments, reduced heterologous protein expression results from by alternate translational initiation. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence.

In some embodiments, reduced heterologous protein expression occurs through repeat-induced polymerase slippage. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage includes altering extended repeats of G or C nucleotides.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

Optimizing a DNA sequence can negatively or positively affect gene expression or protein production. For example, modifying a less-common codon with a more common codon may affect the half life of the mRNA or alter its structure by introducing a secondary structure that interferes with translation of the message. It may therefore be necessary, in certain instances, to alter the optimized message.

AUG or a portion of a gene can be optimized. In some embodiments, the desired modulation of expression is achieved by optimizing essentially the entire gene. In other embodiments, the desired modulation will be achieved by optimizing part but not all of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria can include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

Promising candidate sequences are constructed and then evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation can be included.

Modifying the codon usage of a candidate sequence can result in the creation or destruction of either a positive or negative element. In general, a positive element refers to any element whose alteration or removal from the candidate sequence could result in a decrease in expression of the therapeutic protein, or whose creation could result in an increase in expression of a therapeutic protein. For example, a positive element can include an enhancer, a promoter, a downstream promoter element, a DNA binding site for a positive regulator (e.g., a transcriptional activator), or a sequence responsible for imparting or modifying an mRNA secondary or tertiary structure. A negative element refers to any element whose alteration or removal from the candidate sequence could result in an increase in expression of the therapeutic protein, or whose creation would result in a decrease in expression of the therapeutic protein. A negative element includes a silencer, a DNA binding site for a negative regulator (e.g., a transcriptional repressor), a transcriptional pause site, or a sequence that is responsible for imparting or modifying an mRNA secondary or tertiary structure. In general, a negative element arises more frequently than a positive element. Thus, any change in codon usage that results in an increase in protein expression is more likely to have arisen from the destruction of a negative element rather than the creation of a positive element. In addition, alteration of the candidate sequence is more likely to destroy a positive element than create a positive element. In some embodiments, a candidate sequence is chosen and modified so as to increase the production of a therapeutic protein. The candidate sequence can be modified, e.g., by sequentially altering the codons or by randomly altering the codons in the candidate sequence. A modified candidate sequence is then evaluated by determining the level of expression of the resulting therapeutic protein or by evaluating another parameter, e.g., a parameter correlated to the level of expression. A candidate sequence which produces an increased level of a therapeutic protein as compared to an unaltered candidate sequence is chosen.

In some embodiments, one or a group of codons can be modified, e.g., without reference to protein or message structure and tested. Alternatively, one or more codons can be chosen on a message-level property, e.g., location in a region of predetermined, e.g., high or low GC content, location in a region having a structure such as an enhancer or silencer, location in a region that can be modified to introduce a structure such as an enhancer or silencer, location in a region having, or predicted to have, secondary or tertiary structure, e.g., intra-chain pairing, inter-chain pairing, location in a region lacking, or predicted to lack, secondary or tertiary structure, e.g., intra-chain or inter-chain pairing. A particular modified region is chosen if it produces the desired result.

Methods which systematically generate candidate sequences are useful. For example, one or a group, e.g., a contiguous block of codons, at various positions of a synthetic nucleic acid sequence can be modified with common codons (or with non common codons, if for example, the starting sequence has been optimized) and the resulting sequence evaluated. Candidates can be generated by optimizing (or de-optimizing) a given "window" of codons in the sequence to generate a first candidate, and then moving the window to a new position in the sequence, and optimizing (or de-optimizing) the codons in the new position under the window to provide a second candidate. Candidates can be evaluated by determining the level of expression they provide, or by evaluating another parameter, e.g., a parameter correlated to the level of expression. Some parameters can be evaluated by inspection or computationally, e.g., the possession or lack thereof of high or low GC content; a sequence element such as an enhancer or silencer; secondary or tertiary structure, e.g., intra-chain or inter-chain paring.

In some embodiments, the optimized nucleic acid sequence can express the variant xylanase polypeptide of the invention, at a level which is at least 110%, 150%, 200%, 500%, 1,000%, 5,000% or even 10,000% of that expressed by nucleic acid sequence that has not been optimized.

Starting with the amino acid sequence of a variant xylanase, a candidate DNA sequence can be designed. During the design of the synthetic DNA sequence, the frequency of codon usage can be compared to the codon usage of the host expression organism and rare host codons can be modified in the synthetic sequence. Additionally, the synthetic candidate DNA sequence can be modified in order to remove undesirable enzyme restriction sites and add or alter any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In some embodiments, the general codon usage in a host organism, such as any of those described herein, can be utilized to optimize the expression of the heterologous polynucleotide sequence in the host organism. The percentage and distribution of codons that rarely would be considered as preferred for a particular amino acid in the host expression system can be evaluated. Values of 5% and 10% usage can be used as cutoff values for the determination of rare codons.

VII. Host Cells and Production Strains

As will be appreciated by those in the art, there are a wide variety of production host organisms for the recombinant production of the variant xylanases of the invention, including, but not limited to bacterial cells and fungal cells including yeast. In addition, while the parent xylanase is unglycoslyated, glycosylation by production in yeast and fungi does not adversely affect the xylanase activity.

The present invention also relates to recombinant host cells, comprising a polynucleotide encoding a variant xylanase of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source. In some embodiments, the host cell exhibits transitory expression of the variant xylanase. In some embodiments, the host cell is a stably transfected host or a host cell that stably (i.e., permanently) expresses the variant xylanase. In some embodiments, the host cell is a production cell.

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla *Ascomycota, Basidiomycota, Chytridiomycota*, and *Zygomycota* as well as the *Oomycota* and all mitosporic fungi (as defined by Hawksworth et al., In, Ainsworth and Bisby's Dictionary of The Fungi, 8th edition, 1995, CAB International, University Press, Cambridge, UK).

The fungal host cell can be a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al, 1984, *Proc. Natl. Acad. Sci. USA* 81: 1470-1474, and Christensen et al., 1988, *BiolTechnology* 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, *Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some embodiments, the present invention provides a host cell comprising the nucleic acid as described herein.

In some embodiments, the present invention provides a host cell comprising the expression vector as described herein.

In some embodiments, the present invention provides a host cell comprising the nucleic acid as described herein, wherein the host cell is selected from the group consisting of a bacterial cell, a fungal cell, and a yeast cell.

In some embodiments, the present invention provides a host cell comprising the expression vector as described herein, wherein the host cell is selected from the group consisting of a bacterial cell, a fungal cell, and a yeast cell.

VIII. Compositions

The present invention also provides compositions comprising the variant xylanases as described herein. In some embodiments, the composition further comprises animal feed. In some embodiments, the composition comprises a carrier and/or an excipient. In some embodiments, the compositions are enriched in such a variant xylanase polypeptide of the present invention. The term "enriched" indicates that the xylanase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant xylanase polypeptide of the present invention as the major enzymatic component, e.g., a mono-component composition. In some embodiments, the composition may comprise multiple enzymatic activities, such as an aminopeptidase, alpha-amylase, beta-amylase, isoamylase, carbohydrase, carboxypeptidase, catalase, cellulase, chitinase, cutinase, cydodextrin glycosyltransferase, deoxyribonuclease, esterase, alpha-galactosidase, beta-galactosidase, phytase, alpha-glucosidase, beta-glucosidase, haloperoxidase, invertase, laccase, lipase, mannosidase, oxidase, pectinolytic enzyme, peptidoglutaminase, peroxidase, polyphenoloxidase, pullulanase, proteolytic enzyme, ribonuclease, and/or transglutaminase.

IX. Methods of Production

The present invention also relates to methods of producing a variant xylanase polypeptide, comprising: (a) culturing the host cell of the present invention as described herein under conditions wherein said variant xylanase polypeptide is expressed; and (b) optionally recovering the variant xylanase polypeptide.

The host cells are cultivated in a nutrient medium suitable for production of the variant xylanase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant xylanase polypeptide is secreted into the nutrient medium, the variant xylanase polypeptide can be recovered directly from the medium. If the variant is not secreted, it can be recovered from cell lysates.

The variant xylanase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant xylanase polypeptide.

The variant xylanase polypeptide can be recovered using methods known in the art. For example, the variant xylanase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant. In a particular embodiment, a variant xylanase of the invention is not recovered, and the host cell is a yeast host cell. In particular, the yeast is a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell. In some embodiments, the yeast is *Saccharomyces cerevisiae*.

X. Xylanase Formulations and Uses

As discussed herein, xylanase can break the feed ingredient arabinoxylan, decrease the content of non-starch polysaccharides and reduce the raw material viscosity. Therefore, the use of xylanase in animal feeds has a number of benefits, including increasing the digestibility and nutritive value of poorly degradable feeds such as barley and wheat and improving the utilization of proteins and starch present in the feed.

In some embodiments, the variant xylanases of the invention are formulated and added to feed or can be made as a component of the feed. In the former case, the feed stock addition of xylanase can be done by formulating the xylanase on a carrier feed such as wheat flour.

In some embodiments, the present inveniton provides a formulation suitable for consumption by an animal, wherein said formulation comprises the variant xylanase enzyme as described herein and one or more consumable components.

As will be appreciated by those in the art, the formulation of the variant xylanases of the invention depends on its end use and the associated conditions. Suitable formulations for the variant xylanases of the invention include liquid formulations, dried formulations (including spray dried formulations), powdered formulations, granular formulations, and pelleted formulations.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

The above compositions are suitable for use in liquefaction, saccharification, and/or fermentation processes.

In some embodiments, the above compositions are used in animal feed application. In one embodiment, the xylanases are added to animal feed stock and pelleted as is known in the art, such that the feed is formed with xylanase in it. In other embodiments, the xylanase can be sprayed or closed in a liquid form into animal feed.

In some embodiments, the present invention provides a method of preparing animal feed comprising adding the variant xylanase enzyme as described herein to said animal feed to produce a xylanase-animal feed combination, and heat sterilizing said xylanase-animal feed combination. In some embodiments, the animal feed is a poultry or swine feed.

EXAMPLES

XI. Example 1: Design and Construction of Xylanase Collections

The wild-type xylanase, or G1P, from *Neocallimastix patriciarum* was obtained by gene synthesis from GeneWiz (www.genewiz.com/). To further improve the activity, pH stability, thermostability, and low pH activity, multiple variant collections were designed based sequence and structure analysis. The design includes one to multiple specific mutations per variant. The variant collections were subsequently constructed using standard site-directed mutagenesis methods and subsequently cloned into the pESC-URA vector (Agilent Technologies: catalogue #217454).

XII. Example 2: Preparation of Xylanase Produced by *Saccharomyces cerevisiae* in HTP The Recombinant xylanase-encoding genes from single colonies of the *Saccharomyces cerevisiae* INVSc1 strain (ThermoFisher Scientific, USA: Catalogue #V8251-20) were inoculated into 350 μL Synthetic Minimal Medium with 2% Glucose and no uracil supplementation in 96-well plates. Following induction, the plates were incubated overnight at 30° C., in 85% humidity while shaking at 200 rpm. The $OD_{600}$ of the overnight cultures was determined and all cultures were diluted to a final $OD_{600}$ of 0.4 into fresh 96-well plates containing SC selective medium supplemented with 1% galactose and 0.5% raffinose in a total volume of 300 μL. The induction plates were incubated at 30° C., in 85% humidity while shaking at 200 rpm for 72 h upon which the plates cells were pelleted by centrifugation at 4000 rpm for 15 minutes while chilled to 4° C. The supernatant was transferred to fresh 96-well plates, covered, and stored at −20° C. until further use.

XIII. Example 3: Enzymatic Assay to Determine the pH 5.5 or Low pH Activity at 37° C. of *Saccharomyces cerevisiae* Produced Xylanase WT and Variants in HTP Plates containing WT and/or variants of xylanase produced according to Example 2 were thawed. The supernatant was diluted 175-fold into 0.1 M sodium acetate buffer (pH 5.5) for activity assays at pH 5.5. Supernatant was diluted 20-80-fold (depending on the plate) into 0.1 M citrate-phosphate buffer (pH 3.0) for assays to measure pH 3 activity of xylanase, or into a pH 2.5 HCl solution (89 mmol NaCl, 6.6 mmol KCl).

A 1% xylan solution was prepared by dissolving 1.00 g of xylan (corncob, Shanghai Yuanye Bio-Technology Co., Ltd. Supplier #S25540) and 0.320 g sodium hydroxide in 50 mL deionized water, followed by stirring while heated to 100° C. until the xylan was fully dissolved. The xylan substrate was subsequently adjusted to the desired pH. Either pH 5.5 using acetic acid, or pH 3.0 and pH 2.5 with HCl, followed by volume adjustment to 100 mL utilizing 0.1 M sodium acetate buffer (pH 5.5), 0.1 M citrate-phosphate buffer (pH 3.0), or pH 2.5 HCl solution, respectively.

For all assays, low pH, and pH 5.5, the respective 1% xylan substrate solution was added to 96-well PCR plates (35 μL/well). The reaction was initiated by addition of 35 μL of the diluted enzyme in either low pH or pH 5.5 buffer, as described in this example, to plates containing the same pH 1% xylan solution. The plates were then sealed, incubated at 37° C. shaking at 200 rpm for 2 hours. Following incubation, the reactions were quenched by addition of 80 μL DNS (dinitrosalicylic acid) reagent.

The DNS reagent was prepared by addition of 3.15 g 3,5-dinitrosalicylic acid to 500 mL of water while stirring and heating to 45° C. Next, 100 mL of 200 g/L sodium hydroxide solution was slowly added to the stirring solution until fully transparent. Once transparent, 91.0 g potassium sodium tartrate tetrahydrate, 2.50 g phenol, and 2.50 g anhydrous sodium sulfite were added to the stirring solution, followed by 300 mL of water. The solution was cooled to room temperature and the volume adjusted to 1000 mL, filtered and stored for 7 days prior to use in a non-transparent bottle.

The plates after DNS reagent addition were sealed, heated to 95° C. for 5 min using a thermocyder, cooled to 4° C. for 2 min, mixed by inverting 5-6 times, and then centrifuged for 30 s at 1000 rpm. The assay plates were unsealed and 100 μL from each well was transferred to new clear-bottom plates containing 100 μL water and thoroughly mixed. The absorbance of each well was measured at 540 nm and absorbance values indicated enzyme activity in each well. Variant enzyme activity at low pH (pH 2.5 or 3) or pH 5.5 was compared to the WT (G1P) or G2P enzyme at the same pH to determine activity improvement at the respective pH. The results are shown in FIGS. 1 and 2.

XIV. Example 4: Enzymatic Assay to Determine pH 3 Stability of *Saccharomyces cerevisiae* Produced Xylanase WT and Variants in HTP Plates containing WT and/or variants of xylanase produced according to Example 2 were thawed. The supernatant plates for the G1P based variants were diluted 10, 20, or 30-fold into 0.1 M pH 3.0 citrate-phosphate buffer in non-binding polystyrene 96-well plates (Corning Inc. product #3641) with a total volume of 100 μL per well. The plates at pH 3.0 were incubated for 2 h, 37° C. while shaking at 200 rpm. After incubation was complete the enzymes were diluted a further 2.5-fold into 0.25 M sodium acetate buffer (pH 5.5) to a total volume of 35 μL in 96-well PCR plates. The reaction was initiated by addition of 35 μL/well of 1% xylan solution (prepared as described in Example 3) at pH 5.5. The plates were then sealed, incubated at 37° C. shaking at 200 rpm for 2 hours.

The supernatant plates for the G2P based variants were diluted 20-fold into 0.1 M pH 3.0 citrate-phosphate buffer in non-binding polystyrene 96-well plates (Corning Inc. product #3641) with a total volume of 100 μL per well. The plates at pH 3.0 were incubated for 2 h, 37° C. while shaking at 200 rpm. After incubation was complete the enzymes were diluted a further 8-fold into 0.1 M sodium acetate buffer (pH 5.5) in new 96-well plates. The reaction was initiated after the second dilution by transfer of 35 μL from each well to 96-well PCR plates containing 35 μL/well of 1% xylan solution (prepared as described in Example 3) at pH 5.5. The plates were then sealed, incubated at 37° C. shaking at 200 rpm for 2 hours.

Following incubation, the reactions for both the G1P and G2P comparisons were quenched by addition of 80 μL DNS reagent as described in Example 3. Once quenched the reaction plates were sealed, heated to 95° C. for 5 min, cooled to 4° C. for 2 min, mixed by 5-6 inversions, and then centrifuged for 30 s at 1000 rpm. The assay plates were unsealed and 100 μL from each well was transferred to new clear-bottom plates containing 100 μL water and thoroughly mixed. The absorbance of each well was measured at 540 nm and absorbance values indicated enzyme activity in each well. Variant enzyme activity after the low pH incubation was compared to the WT (G1P) or G2P to determine low pH stability improvement. The results are shown in FIGS. 1 and 2.

XV. Example 5: Enzymatic Assay to Determine Thermostability of *Saccharomyces cerevisiae* Produced Xylanase WT and Variants at 90° C. for 15 Minutes in HTP Thawed plates of WT and/or variant xylanase produced according to Example 2 were diluted 4.5-fold into 0.1 M pH 5.5 sodium acetate buffer in a 96-well PCR plate. The remaining enzyme at 4.5-fold diluted was incubated at 90° C. for 15 min or 5 min, followed by chilling to 4° C. for 2 minutes in a thermocyder. The thermo challenged enzymes were diluted 20-fold into 0.1 M pH 5.5 sodium acetate buffer in a new 96-well plate.

Diluted enzyme (35 μL) was then added to separate 96-well PCR plates containing 35 μL of 1% xylan substrate (pH 5.5) prepared as described in Example 3. The plates were then sealed, incubated at 37° C. shaking at 200 rpm for 2 hours. Following incubation, the reactions were quenched by addition of 80 μL DNS reagent as described in Example 3.

Upon DNS addition the plates were sealed, heated to 95° C. for 5 min, cooled to 4° C. for 2 min, mixed by 5-6 inversions, then centrifuged for 30 s at 1000 rpm. The absorbance of each well was measured at 540 nm indicating enzyme activities.

Variant enzyme after thermostability challenge was compared to the WT (G1P) or G2P enzyme at the same pH to determine activity improvement at the respective pH. The results are shown in FIGS. 1 and 2.

The examples set forth above are provided to give those of ordinary skill in the art a complete disclosure and description of how to make and use the embodiments of the compositions, systems, and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

We claim:
1. A composition comprising:
a variant xylanase enzyme comprising: at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, and wherein said variant enzyme is at least 90% identical to SEQ ID NO:1, and wherein the amino acid substitution at the position number of 160 is N160Q or N160R;
a variant xylanase enzyme comprising: at least two amino acid substitutions as compared to SEQ ID NO:1 comprising an amino acid substitution at position number

18 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant enzyme is at least 90% identical to SEQ ID NO:1, and wherein the amino acid substitution at the position number of 160 is N160Q or N160R;

a variant xylanase enzyme comprising: at least two amino acid substitutions as compared to SEQ ID NO:1 comprising an amino acid substitution at position number 160 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1; or a variant xylanase enzyme comprising: at least three amino acid substitutions as compared to SEQ ID NO 1, comprising an amino acid substitution at position number 18, an amino acid substitution at position number 160, and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1; and further comprising an amino acid substitution at position 131 which is H131F.

2. The composition according to claim 1, wherein said variant xylanase enzyme exhibits at least 95% identity to SEQ ID NO:1.

3. The composition according to claim 1, wherein said amino acid substitution(s) occur at one of said positions, two of said positions, three of said positions, four of said positions, five of said positions, six of said positions, seven of said positions, eight of said positions, nine of said positions, ten of said positions, or eleven of said positions.

4. The composition according to claim 1, wherein said amino acid substitution(s) is selected from the group consisting of Q1H, Q1P, S2K, S51, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V27I, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S90I, G93L, V99A, V99G, S105D, S105H, S105I, S105N, P119Q, F120D, F120H, F120S, F120Y, P121G, P121R, H131P, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

5. The composition according to claim 1, wherein said amino acid substitutions are selected from the group consisting of S51, T51C, K15T, G25E, S5K, T51E, K20C, T51R, Q1P, T51Q, S8C, K20V, Q12T, G26C, S8H, K20S, K15R, Q12L, S6K, Q1H, S8R, K15H, S5R, G26T, G26N, K15V, S6T, S6H, G26R, V27W, T149R, G224K, D225Y, N160Q, T190P, G224L, G224M, G224T, Q168S, T190H, N160R, S105D, G56R, S901, F120Y, N54D, S89C, F120H, G56T, S90C, S105H, V99A, G56H, S89V, S133L, S90E, V99G, S133T, S90A, S90F, S133K, N54G, S89A, G93L, F120D, S89T, S105I, S105N, P121G, F120S, G56K/ P119Q, G56K/F120Y/S133D, G56K/S178T, T51S/S133D, V271/G56K/N160K, P121R/S133D/N160K, G18S/V271/ G56K/N160K/L194M, G18S/G28D, G56K/P119Q/P121R/ S133D/L194M, G18S/G56K/F120Y, V271/N160K, T51S/ P119Q/S133D/N160K/S178T, G18S/T23S/G56K/P119Q/ F120Y/P121R/S133D, T51S/F120Y, G56K/S133D/N160K, T51S/G56K/F120Y/S178T, G56K/N160K, T51S/G56K/ S133D/N160K, T51S/P119Q/F120Y/N160K, Q1P/S8R/ K20V/T51C/S89C/S90H, Q1P/S8H/K20V, Q1P/K15T/ K20C/V27W/V99A, S8C/K20V/V27W/H131F, S8H/ H131F, V27W/H131F, Q1P/K20C/V27W, K15T/K20V/ V27W, K20C/V27W/S89V/S90H, Q1P/S8H/K15T/V27W/ H131F, Q1P/S8C/K15T/K20V/V27W/S89T/H131F, Q1P/ S8H/K15H/V27W/H131F, Q1P/S8H/V27W/S89T, Q1P/ S8R/S89A/S90H/H131F, K20V/V27W/T51C/S89C/S90H/ H131F, Q1P/H131F, K15H/K20V/V27W/H131F/G224K, Q1P/S8R/K15T/K20V/V27W/S89A/S90H/V99A/H131F/ G224L, Q1P/S8H/T51C/H131F, Q1P/K20V/V27W/V99A/ H131F, Q1P/S8R/K20V/V27W/T51C/G224L, Q1P/S8R/ K15T/K20C/V27W/S89A/H131F, K15T/K20V/V27W/ H131F, Q1P/S8R/K20C/V27W, S8H/K20V/V27W, Q1P/ S8H/K15H/K20V/V27W/S89C/S90H/V99A/H131F, Q1P/ S8R/K15H/V27W/V99A, K15H/V27W, S90E/H131F, Q1P/ K15H/K20V/V27W/T51C/S90H/H131F, K15T/K20C/ V27W/H131F, V27W/G224L, K20V/V27W/H131F, K15T/ K20V/V27W/T51C/G224L, Q1P/S8C/H131F, Q1P/S8R/ K15H/K20V/V27W/T51C/S90E, Q1P/S8R/V27W, Q1P/ S8C/V27W/T51C/H131F, Q1P/S8H, K15T/K20C/V27W/ S90H/H131F, K15T/V27W/S90H, Q1P/K20V/H131F, K15T/V27W, Q1P/H131F/G224L, S8C/K15T/K20V/ V27W/T51C/S90H, Q1P/K15T/K20C/V27W/T51C/S89C/ S90H/H131F, Q1P/S8H/K20C/V27W, Q1P/S90H/N160K/ T190H, Q1P/S5K/G26N/V27W/F120Y/Q168S/T190H, Q12T/K20C/G26T/S89C/H131F/Q168S, S51/K20S/S89T/ V99A/F120D/H131F/Q168S/T190H, Q1P/S5K/K20S/ S89C/F120Y, S6H/G56K/V99A/Q168S/T190H, S8R/ K20V/T190H, K15T/G26T/G56K/H131F/N160K/T190H, S8H/K20C/S105N/H131F/N160Q/Q168S, Q1H/S5R/ K15V/G56K/Q168S, K20S/G56K/F120Y/N160Q/T190H, S8R/H131F/T190H, G26N/V27W/G56K/S90H/H131F/ Q168S/T190H, S89V/H131F/Q168S, S5R/Q12L/K15T/ G26N/V27W/G56K/F120Y/H131F, S6H/S8R/K20S/S89A/ V99A, Q1P/S5R/G26T/S90C/H131F/Q168S/T190H, S8H/ K20C/T51R/S89A/P121R/N160K/T190H, Q1P/S5R/Q12T/ K15V/G26T/V27W/S90E/H131F/G224K, Q1P/S5R/K20S/ G56K/S89C/H131F/N160K/Q168S/T190H, Q1H/S5K/ Q12L/S90H/S105N/T190H, S8C/K20C/T51C/S89A/ Q168S, G26N/V27W/S105N/Q168S/G224L, S51/S90H/ S105N/F120Y/P121R/H131F/Q168S/G224K, S6H/S8C/ K20S/T51S/F120Y/P121R/T190H, S5K/V99G/T190H, S5K/K20V/G56K/H131F/Q168S, S8R/T51R/S89T/H131F/ T190H, Q1P/S5R/S8R/V99A/N160Q, S8R/T51C/F120D/ Q168S/G224L, Q1P/V27W, Q1P/Q12T/K20V/G56K/ S105N/N160Q/T190H/G224K, Q1H/S51/Q12L/K15R/ H131F, S89C/F120D/H131F/N160Q/G224L, K20C/P121R, K20S/V27W/T51Q/S105N/F120D/P121R/N160Q/T190H/ G224M, Q1H/S8C/K20V/G56K/S89A/H131F/T190H/ G224L, S8H/G26T, S6H/S8C/K20S/S89C/T190H, K20S/ T51C/S89V/T190H, Q1H/Q12L/K15R/V27W/G56K/ V99A/N160K/T190H, S8C/K15R/S105N/H131F/T190H, Q1H/S5R/Q12L/K20C/G56K/H131F/T190H, Q1H/S51/ Q12T/K15V/G26T/G56K/S90E/S105N/Q168S, S6H/ K20C/S89T, Q1H/S5R/K15R/G26N/G56K/H131F/T190H/ G224K, S89V/V99G/T190H, Q1H/S51/Q12L/K15T/ Q168S, Q12L/K15R/S90H/H131F/Q168S/T190H, Q1H/ S51/T190H, Q1P/S8H/K20V/T51Q/S89T/V99A/F120D/ T190H, S8R/K20S/G56K/K86T/S89A/V99A/H131F, S8C/

Q12T/K15V/G56K/T190H, K20S/S89C/F120Y/H131F/T190H, Q1P/K20V/G56K/S90E/S105N/H131F, S51/K20S/G26N/V27W/G56K/S90H/S105N/Q168A/T190H, Q1P/S2K/S6H/S8R/S105N/Q168S/G224K, S8H/K20C/T51R/S89A/N160K/Q168S, Q1H/S5R/Q12T/K15R/G26N/S89A/V99G/F120D/P121R/T190H/G224M, S8C/K20S/G56K/S89C/V99G/F120D/P121R/T190H, S6H/S8H/K20C/T51R/S89A/P121R/T190H, Q1P/S5K/T51Q/V99G, Q1P/S51/S89V/S105N/H131F/Q168S, S8H/K15V/K20C/T51Q/S89A/S105N/Q168S, Q1P/S51/K15R/G26T/S89C/V99G/F120Y/N160Q/T190H/G224K, S89C/H131F/Q168S/T190H, Q1P/S5K/Q12L/K20C/T51Q/S89V/F120Y/N160K/Q168S/T190H, Q1H/S5K/G56K/F120D/P121R/Q168S, T51E/V99A/P121R/H131F/N160Q/Q168S/T190H/G224K, Q1P/S5R/Q12T/K15H/G26N/V27W/G56K/S90C/S105N/T190H, S6H/S8R/K20C/T51C/F120D/T190H, S8R/K20S/F120D/P121R, S5R/S105N/Q168S/T190H, Q1H/S5R/K15V/G26N/V27W/H131F/Q168S/T190H, Q1H/S5R/Q12L/K15T/S90E/S105N/H131F/Q168S, K20V/S89V/V99A/N160K/Q168S/G224K, S90C/S105N/H131F, S6H/S8H/K20V/T190H, S8H/T51E/V99G/Q168S/T190H, S5R/Q12L/K20V/S89C/Q168S/T190H, Q1P/S5K/Q12T/K15H/G26N/V27W/G56K/S89C/H131F, K15R/G56K/T190H, Q1H/S5K/Q12T/K15T/G26T/G56K/S89C/H131F/N160K/Q168S, S6H/S8R/K20V/T51E/S90H/S105N/H131F/T135S/Q168S/T190H, Q1P/S5K/Q12L/K15R/G56K/S89T/F120D, Q12L/H131F/N160K/T190H, Q1H/S5R/Q12T/K15H/G26N/V27W/G56K/H131F, Q1P/S5K/Q12T/G56K/S105N/H131F/Q168S/T190H/G224L, V27W/S90C/V99G/S105N/F120Y/N160K/Q168S, G56K/S90C/H131F/Q168S/T190H, Q1P/S5R/G26T/G56K/S105N/H131F/Q168S/T190H, S8C/T51E/S89A/V99A/H131F/Q168S/T190H, S5K/K15H/G26T/S90H/H131F, G26N/G56K/S89T/H131F/Q168S/T190H/G224K, Q1P/Q12L/K15T/G26N/V27W/S90H/S105N/H131F/T190H, G56K/S90C, K20S/S89V/V99G/S105N/T190H, S51/G26N/G56K/V99G/S105N, Q1P/S5R/G56K/H131F/N160K/T190H, Q1H/S51/K20V/S89C, K20C/T51Q/S89C/V99G/F120D/P121R/T190H, S8R/Q12T/K15V/T51E/S89A/V99A/F120D/P121R/T190H, G26N/V27W/S105N/H131F/Q168S, S6H/S89T/V99A/F120D/P121R/N160Q/Q168S/T190H, T51Q/H131F, Q1P/S5R/Q12L/K15V/V27W/G56K/V99A/S105N/F120D/N160Q/Q168S, Q1P/S5R/G26N/G56K/S90H/S105N/F120D/P121R/T190H, S5R/Q12T/K20V/G56K/F120Y, S105N/F120D/P121R/T190H, S8R/K20C/G26N/V27W/G56K/H131F/T190H, Q1H/V27W/G56K/S90C, G56K/S90C/H131F/Q168S/T190H, Q12L/K15R/V27W/G56K/S90E, Q1H/S105N/T190H, G56K/S89T/S105N/P121R/H131F/Q168S/G224K, K20S/S89A/V99G/S105N/N160Q/T190H, Q1P/P121R/H131F/N160Q/T190H, K15V/T51Q/S89V/H131F/G224K, Q1P/K20S/N160K/T190H, S8H/G56K/S89V/F120Y/P121R/N160Q/Q168S/T190H, Q1H/S5K/V27W/G56K/Q168S/T190H, F120D/P121R/Q168S, S8H/K20V/T51S/V99A/T190H, S8R/T51E/S89T/V99G/N160K/T190H, K20S/S89C/T190H, K20S/S90E/G224M, K15V/G56K/S89T/T190H, S6H/S8R/Q12L/K15V/G26T/V27W/G56K/Q168S, Q1P/S51/K20S/G56K/S90E/H131F/Q168S, S6H/F120Y/T190H, S8H/K20V/T51S, S105N/H131F, S51/Q12T/K15H/G26T/V27W/G56K/S90H/S105N/H131F/N160K/T190H, Q1H/S5R/G26T/G56K/S105N/H131F/G224K, S51/S89C/S105N/H131F/Q168S, Q1P/S5R/Q12L/K15R/G56K/S90H/F120D/P121R/H131F/N160K, S105N/H131F/Q168S, S6H/S8R/K20V/G56K/F120D/P121R/H131F/T190H, Q1P/S51/G26N/V27W/S90E/H131F/Q168S/G224M, G56K/T190H, S8R/K20C/T51E/S89V/Q168S/G224M, S8C/K20S/S89A/F120Y/P121R/N160Q, S5R/S89T/F120Y/P121R/T190H, G26N/V27W/G56K/S105N/H131F/Q168S, S6H/S8R/S89A/F120Y, Q1P/S5R/Q12L/K15R/G26T/S90H/Q168S/T190H, K20C/H131F, K20C/V27W/H131F, K15H/K20C/H131F, K15H/K20V/V27W/S89A/H131F, K15H/S89C/H131F, K15H/V27W/H131F, K15R/K20C/H131F, K15R/K20C/S89A/H131F, K15R/K20C/S89C/H131F, K15R/K20C/S89V/H131F, K15R/K20V/H131F, K15R/S89A/H131F, K15R/S89C/H131F, K15R/S89V/H131F, K20C/H131F, K20C/S89T/H131F, K20C/V27W/S89T/H131F/E185K, K20V/H131F, K20V/S89C/H131F, K20V/S89T/H131F, K20V/S89V/H131F, S89A/H131F, S89C/H131F, S8C/K15H/K20C/S89T/H131F, S8C/K20C/H131F, S8C/K20V/S89C/H131F, S8C/K20V/S89T/H131F, S8H/K15R/K20C/S89T/H131F, S8H/K20C/S89T/H131F, S8H/K20C/V27W/H131F, S8H/K20V/H131F, S8H/K20V/S89C/H131F, S8H/K20V/V27W/S89T/H131F, S8R/K15H/K20V/S89C/H131F, S8R/K15R/K20C/H131F, S8R/K20C/S89C/H131F, V27W/S89C/H131F, V27W/S89T/H131F, G26T/V27W/H131F, V27W/S89A/H131F, V27W/H131F/S133T, G26T/V27W/S89A/H131F, G26T/V27W/H131F/S133T, V27W/S89A/H131F/S133T, G26T/V27W/S89A/H131FS/S133T, G26T/V27W/S35R/S89A/H131FS/S133R, and V27W/N38Y/F52W/G56Y/H131F/G201L.

6. The composition according to claim 1, wherein said variant xylanase enzyme has at least 95% sequence identity to the amino acid sequence of SEQ ID NO:3 or SEQ ID NO:5.

7. The composition according to claim 1, wherein said amino acid substitutions are V27W/H131F.

8. The composition according to claim 1 comprising an amino acid substitution H131F, and further comprising at least one amino acid substitution selected from the group consisting of Q1H, Q1P, S2K, S51, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, V271, V27W, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S901, G93L, V99A, V99G, S105D, S105H, S1051, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

9. The composition according to claim 1 comprising amino acid substitutions V27W/H131F, and further comprising at least one amino acid substitution selected from the group consisting of Q1H, Q1P, S2K, S51, S5K, S5R, S6H, S6K, S6T, S8C, S8H, S8R, Q12L, Q12T, K15H, K15R, K15T, K15V, G18S, K20C, K20S, K20V, T23S, G25E, G26C, G26N, G26R, G26T, G28D, S35R, N38Y, T51C, T51E, T51Q, T51R, T51S, F52W, N54D, N54G, G56H, G56K, G56R, G56T, G56Y, K86T, S89A, S89C, S89T, S89V, S90A, S90C, S90E, S90F, S90H, S901, G93L, V99A, V99G, S105D, S105H, S1051, S105N, P119Q, F120D, F120H, F120S, F120Y, P121G, P121R, S133D, S133K, S133L, S133T, S133R, T135S, T149R, N160K, N160Q, N160R, Q168S, Q168A, S178T, E185K, T190H, T190P, L194M, G201L, G224K, G224L, G224M, G224T, and D225Y.

10. The composition according to claim 1 further comprising animal feed.

11. A formulation suitable for consumption by an animal, wherein said formulation comprises the variant xylanase enzyme of claim 1 and one or more consumable components.

12. A method of preparing animal feed comprising adding the variant xylanase enzyme of claim 1 to said animal feed to produce a xylanase-animal feed combination, and heat sterilizing said xylanase-animal feed combination.

13. The method of claim 12, wherein said animal feed is a poultry or swine feed.

14. The composition according to claim 1 comprising the variant xylanase enzyme comprising: at least one amino acid substitution as compared to SEQ ID NO:1, wherein said amino acid substitution is at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225 wherein said variant enzyme is at least 90% identical to SEQ ID NO:1, and wherein the amino acid substitution at the position number of 160 is N160Q or N160R.

15. The composition according to claim 1 comprising the variant xylanase enzyme comprising: at least two amino acid substitutions as compared to SEQ ID NO:1 comprising an amino acid substitution at position number 18 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant enzyme is at least 90% identical to SEQ ID NO:1, and wherein the amino acid substitution at the position number of 160 is N160Q or N160R.

16. The composition according to claim 1 comprising the variant xylanase enzyme comprising: at least two amino acid substitutions as compared to SEQ ID NO:1 comprising an amino acid substitution at position number 160 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1.

17. The composition according to claim 1 comprising a variant xylanase enzyme comprising: at least three amino acid substitutions as compared to SEQ ID NO 1, comprising an amino acid substitution at position number 18, an amino acid substitution at position number 160, and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1.

18. A nucleic acid encoding a variant xylanase enzyme comprising: at least one amino acid substitution as compared to SEQ ID NO:1, wherein said amino acid substitution is at a position number selected from the group consisting of 1, 2, 5, 6, 8, 12, 15, 18, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, and wherein said variant enzyme is at least 90% identical to SEQ ID NO:1, and wherein the amino acid substitution at the position number of 160 is N160Q or N160R;

a variant xylanase enzyme comprising: at least two amino acid substitutions as compared to SEQ ID NO:1 comprising an amino acid substitution at position number 18 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 160, 168, 178, 185, 190, 194, 201, 224, and 225, wherein said variant enzyme is at least 90% identical to SEQ ID NO:1, and wherein the amino acid substitution at the position number of 160 is N160Q or N160R;

a variant xylanase enzyme comprising: at least two amino acid substitutions as compared to SEQ ID NO:1 comprising an amino acid substitution at position number 160 and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1; or a variant xylanase enzyme comprising: at least three amino acid substitutions as compared to SEQ ID NO 1, comprising an amino acid substitution at position number 18, an amino acid substitution at position number 160, and at least one more amino acid substitution at a position number selected from the group consisting of 1, 2, 5, 6, 8, 12, 15, 20, 23, 25, 26, 27, 28, 35, 38, 51, 52, 54, 56, 86, 89, 90, 93, 99, 105, 119, 120, 121, 131, 133, 135, 149, 168, 178, 185, 190, 194, 201, 224, and 225, wherein said variant enzyme is at least 90% identical to SEQ ID NO:1; and further comprising an amino acid substitution at position 131 which is H131F.

19. The nucleic acid of claim 18, wherein said nucleic acid is codon optimized for a host organism for expression of the variant xylanase enzyme in said organism.

20. The nucleic acid of claim 18 comprising a sequence that has at least 80% sequence identity to the sequence of SEQ ID NO:4 or SEQ ID NO:6.

21. The nucleic acid of claim 18 comprising the sequence of SEQ ID NO:4 or SEQ ID NO:6.

22. An expression vector comprising the nucleic acid of claim 18.

23. A host cell comprising the expression vector of claim 22.

24. The host cell of claim 23, wherein said host cell is selected from the group consisting of a bacterial cell, a fungal cell, and a yeast cell.

25. A method of making a variant xylanase enzyme comprising: a) culturing the host cell of claim 23 under conditions wherein said variant xylanase enzyme is expressed; and b) recovering said variant xylanase enzyme.

26. A host cell comprising the nucleic acid claim 18.

27. The host cell of claim 26, wherein said host cell is selected from the group consisting of a bacterial cell, a fungal cell, and a yeast cell.

28. A method of making a variant xylanase enzyme comprising: a) culturing the host cell of claim 26 under conditions wherein said variant xylanase enzyme is expressed; and b) recovering said variant xylanase enzyme.

* * * * *

SEQUENCE LISTING

```
<160> NUMBER OF SEQ ID NOS: 6

<210> SEQ ID NO 1
<211> LENGTH: 225
<212> TYPE: PRT
<213> ORGANISM: Artificial Sequence
<220> FEATURE:
<223> OTHER INFORMATION: Synthetic Sequence_Xylanase G1P (wild-type)
      protein

<400> SEQUENCE: 1

Gln Ser Phe Cys Ser Ser Ala Ser His Ser Gly Gln Ser Val Lys Val
1               5                   10                  15

Thr Gly Asn Lys Val Gly Thr Ile Gly Gly Val Gly Tyr Glu Leu Trp
            20                  25                  30

Ala Asp Ser Gly Asn Asn Ser Ala Thr Phe Tyr Ser Asp Gly Ser Phe
        35                  40                  45

Ser Cys Thr Phe Gln Asn Ala Gly Asp Tyr Leu Cys Arg Ser Gly Leu
    50                  55                  60

Ser Phe Asp Ser Thr Lys Thr Pro Ser Gln Ile Gly Arg Met Lys Ala
65                  70                  75                  80

Asp Phe Lys Leu Val Lys Gln Asn Ser Ser Asn Val Gly Tyr Ser Tyr
                85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Trp Val Gly Asn
        115                 120                 125

Lys Lys His Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Phe Ser Ile Arg Gln Gln Ala Arg Asp Cys Gly Thr Ile Asp
                165                 170                 175
```

```
Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
            195                 200                 205

Gly Ala Ser Gly Thr Ala Asp Phe Pro Tyr Ala Lys Val Tyr Ile Gly
            210                 215                 220

Asp
225

<210> SEQ ID NO 2
<211> LENGTH: 678
<212> TYPE: PRT
<213> ORGANISM: Artificial Sequence
<220> FEATURE:
<223> OTHER INFORMATION: Synthetic Sequence_N.A. encoding Xylanase G1P
      (wild-type) protein

<400> SEQUENCE: 2

Cys Ala Ala Ala Gly Thr Thr Cys Thr Gly Thr Ala Gly Thr Thr
1               5                   10                  15

Cys Ala Gly Cys Thr Thr Cys Thr Cys Ala Cys Thr Cys Thr Gly Gly
            20                  25                  30

Ala Cys Ala Ala Ala Gly Thr Gly Thr Ala Ala Ala Gly Gly Thr Ala
            35                  40                  45

Ala Cys Cys Gly Gly Cys Ala Ala Cys Ala Ala Gly Gly Thr Thr Gly
            50                  55                  60

Gly Ala Ala Cys Thr Ala Thr Gly Gly Thr Gly Gly Thr Gly Thr
65                  70                  75                  80

Thr Gly Gly Thr Thr Ala Cys Gly Ala Ala Thr Thr Ala Thr Gly Gly
            85                  90                  95

Gly Cys Thr Gly Ala Thr Ala Gly Thr Gly Gly Thr Ala Ala Thr Ala
            100                 105                 110

Ala Cys Ala Gly Thr Gly Cys Thr Ala Cys Thr Thr Cys Thr Ala
            115                 120                 125

Thr Thr Cys Thr Gly Ala Thr Gly Gly Thr Thr Cys Cys Thr Thr Cys
            130                 135                 140

Thr Cys Ala Thr Gly Thr Ala Cys Thr Thr Thr Cys Cys Ala Ala Ala
145                 150                 155                 160

Ala Thr Gly Cys Thr Gly Gly Gly Ala Thr Ala Cys Thr Thr
            165                 170                 175

Ala Thr Gly Thr Cys Gly Thr Ala Gly Thr Gly Gly Thr Cys Thr Thr
            180                 185                 190

Thr Cys Thr Thr Thr Cys Gly Ala Thr Ala Gly Thr Ala Cys Thr Ala
            195                 200                 205

Ala Gly Ala Cys Cys Cys Ala Thr Cys Thr Cys Ala Ala Ala Thr
            210                 215                 220

Thr Gly Gly Thr Cys Gly Thr Ala Thr Gly Ala Ala Gly Gly Cys Thr
225                 230                 235                 240

Gly Ala Thr Thr Thr Cys Ala Ala Ala Cys Thr Thr Gly Thr Cys Ala
            245                 250                 255

Ala Ala Cys Ala Ala Ala Thr Ala Gly Thr Thr Cys Cys Ala Ala
            260                 265                 270

Thr Gly Thr Thr Gly Gly Thr Thr Ala Thr Cys Cys Thr Ala Thr
            275                 280                 285

Gly Thr Thr Gly Gly Thr Gly Thr Thr Thr Ala Cys Gly Gly Thr Thr
```

```
                    290                 295                 300
Gly Gly Ala Cys Thr Ala Gly Ala Ala Gly Thr Cys Cys Ala Cys Thr
305                 310                 315                 320

Thr Gly Thr Cys Gly Ala Ala Thr Ala Cys Thr Ala Cys Ala Thr Thr
                325                 330                 335

Gly Thr Cys Gly Ala Thr Ala Ala Thr Thr Gly Gly Cys Thr Thr Ala
                340                 345                 350

Gly Thr Cys Cys Ala Thr Cys Cys Cys Ala Cys Ala Gly Gly
            355                 360                 365

Th

```
<220> FEATURE:
<223> OTHER INFORMATION: Synthetic Sequence_Xylanase G2P protein

<400> SEQUENCE: 3

Gln Ser Phe Cys Ser Ser Ala Ser His Ser Gly Gln Ser Val Lys Val
1               5                   10                  15

Thr Gly Asn Lys Val Gly Thr Ile Gly Val Gly Tyr Glu Leu Trp
            20                  25                  30

Ala Asp Ser Gly Asn Asn Ser Ala Thr Phe Tyr Ser Asp Gly Ser Phe
        35                  40                  45

Ser Cys Thr Phe Gln Asn Ala Gly Asp Tyr Leu Cys Arg Ser Gly Leu
    50                  55                  60

Ser Phe Asp Ser Thr Lys Thr Pro Ser Gln Ile Gly Arg Met Lys Ala
65                  70                  75                  80

Asp Phe Lys Leu Val Lys Gln Asn Ser Ser Asn Val Gly Tyr Ser Tyr
                85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Trp Val Gly Asn
        115                 120                 125

Lys Lys Phe Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Phe Ser Ile Arg Gln Gln Ala Arg Asp Cys Gly Thr Ile Asp
                165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
        195                 200                 205

Gly Ala Ser Gly Thr Ala Asp Phe Pro Tyr Ala Lys Val Tyr Ile Gly
    210                 215                 220

Asp
225

<210> SEQ ID NO 4
<211> LENGTH: 678
<212> TYPE: PRT
<213> ORGANISM: Artificial Sequence
<220> FEATURE:
<223> OTHER INFORMATION: Synthetic Sequence_N.A. encoding Xylanase G2P
      protein

<400> SEQUENCE: 4

Cys Ala Ala Ala Gly Thr Thr Thr Cys Thr Gly Thr Ala Gly Thr Thr
1               5                   10                  15

Cys Ala Gly Cys Thr Thr Cys Thr Cys Ala Cys Thr Cys Thr Gly Gly
            20                  25                  30

Ala Cys Ala Ala Ala Gly Thr Gly Thr Ala Ala Gly Gly Thr Ala
        35                  40                  45

Ala Cys Cys Gly Gly Cys Ala Ala Cys Ala Ala Gly Gly Thr Thr Gly
    50                  55                  60

Gly Ala Ala Cys Thr Ala Thr Thr Gly Gly Thr Gly Thr Gly Gly Thr
65                  70                  75                  80

Thr Gly Gly Thr Thr Ala Cys Gly Ala Ala Thr Thr Ala Thr Gly Gly
                85                  90                  95
```

-continued

```
Gly Cys Thr Gly Ala Thr Ala Gly Gly Thr Ala Ala Thr Ala
            100                 105                 110

Ala Cys Ala Gly Thr Gly Cys Thr Ala Cys Thr Thr Cys Thr Ala
        115                 120                 125

Thr Thr Cys Thr Gly Ala Thr Gly Gly Thr Thr Cys Cys Thr Thr Cys
    130                 135                 140

Thr Cys Ala Thr Gly Thr Ala Cys Thr Thr Thr Cys Ala Ala Ala
145                 150                 155                 160

Ala Thr Gly Cys Thr Gly Gly Gly Ala Thr Thr Ala Cys Thr Thr
            165                 170                 175

Ala Thr Gly Thr Cys Gly Thr Ala Gly Thr Gly Gly Thr Cys Thr Thr
            180                 185                 190

Thr Cys Thr Thr Thr Cys Gly Ala Thr Ala Gly Thr

```
                515                 520                 525
Ala Thr Thr Thr Cys Thr Gly Cys Thr Cys Ala Cys Thr Thr Thr Gly
            530                 535                 540
Ala Thr Cys Ala Ala Thr Gly Gly Gly Ala Ala Ala Gly Cys Thr
545                 550                 555                 560
Thr Gly Gly Thr Ala Thr Gly Ala Cys Thr Ala Thr Gly Gly Gly Thr
                565                 570                 575
Ala Ala Ala Thr Ala Cys Ala Thr Gly Ala Ala Gly Cys Cys Ala
            580                 585                 590
Ala Gly Gly Thr Thr Thr Ala Gly Gly Thr Gly Ala Ala Gly Cys
        595                 600                 605
Cys Gly Gly Thr Ala Ala Cys Gly Thr Thr Ala Cys Gly Gly Thr
    610                 615                 620
Gly Gly Thr Gly Cys Cys Ala Gly Thr Gly Gly Thr Ala Cys Cys Gly
625                 630                 635                 640
Cys Thr Gly Ala Thr Thr Thr Cys Cys Ala Thr Ala Cys Gly Cys
                645                 650                 655
Ala Ala Ala Gly Gly Thr Thr Thr Ala Cys Ala Thr Gly Gly Thr
            660                 665                 670
Gly Ala Thr Thr Ala Gly
        675

<210> SEQ ID NO 5
<211> LENGTH: 225
<212> TYPE: PRT
<213> ORGANISM: Artificial Sequence
<220> FEATURE:
<223> OTHER INFORMATION: Synthetic Sequence_Xylanase G3P protein

<400> SEQUENCE: 5

Gln Ser Phe Cys Ser Ser Ala Ser His Ser Gly Gln Ser Val Lys Val
1               5                   10                  15

Thr Gly Asn Lys Val Gly Thr Ile Gly Gly Trp Gly Tyr Glu Leu Trp
            20                  25                  30

Ala Asp Ser Gly Asn Asn Ser Ala Thr Phe Tyr Ser Asp Gly Ser Phe
        35                  40                  45

Ser Cys Thr Phe Gln Asn Ala Gly Asp Tyr Leu Cys Arg Ser Gly Leu
    50                  55                  60

Ser Phe Asp Ser Thr Lys Thr Pro Ser Gln Ile Gly Arg Met Lys Ala
65                  70                  75                  80

Asp Phe Lys Leu Val Lys Gln Asn Ser Ser Asn Val Gly Tyr Ser Tyr
                85                  90                  95

Val Gly Val Tyr Gly Trp Thr Arg Ser Pro Leu Val Glu Tyr Tyr Ile
            100                 105                 110

Val Asp Asn Trp Leu Ser Pro Phe Pro Pro Gly Asp Trp Val Gly Asn
        115                 120                 125

Lys Lys Phe Gly Ser Phe Thr Ile Asp Gly Ala Gln Tyr Thr Val Tyr
    130                 135                 140

Glu Asn Thr Arg Thr Gly Pro Ser Ile Asp Gly Asp Thr Thr Phe Asn
145                 150                 155                 160

Gln Tyr Phe Ser Ile Arg Gln Gln Ala Arg Asp Cys Gly Thr Ile Asp
                165                 170                 175

Ile Ser Ala His Phe Asp Gln Trp Glu Lys Leu Gly Met Thr Met Gly
            180                 185                 190

Lys Leu His Glu Ala Lys Val Leu Gly Glu Ala Gly Asn Val Asn Gly
```

```
                195                 200                 205
Gly Ala Ser Gly Thr Ala Asp Phe Pro Tyr Ala Lys Val Tyr Ile Gly
    210                 215                 220
Asp
225

<210> SEQ ID NO 6
<211> LENGTH: 678
<212> TYPE: PRT
<213> ORGANISM: Artificial Sequence
<220> FEATURE:
<223> OTHER INFORMATION: Synthetic Sequence_N.A. encoding Xylanase G3P
      protein

<400> SEQUENCE: 6

Cys Ala Ala Ala Gly Thr Thr Cys Thr Gly Thr Ala Gly Thr Thr
1               5                   10                  15
Cys Ala Gly Cys Thr Thr Cys Thr Cys Ala Cys Thr Cys Thr Gly Gly
                20                  25                  30
Ala Cys Ala Ala Ala Gly Thr Gly Thr Ala Ala Ala Gly Gly Thr Ala
                35                  40                  45
Ala Cys Cys Gly Gly Cys Ala Ala Cys Ala Ala Gly Gly Thr Thr Gly
            50                  55                  60
Gly Ala Ala Cys Thr Ala Thr Thr Gly Gly Thr Gly Gly Thr Thr Gly
65                  70                  75                  80
Gly Gly Gly Thr Thr Ala Cys Gly Ala Ala Thr Thr Ala Thr Gly Gly
                85                  90                  95
Gly Cys Thr Gly Ala Thr Ala Gly Thr Gly Gly Thr Ala Ala Thr Ala
                100                 105                 110
Ala Cys Ala Gly Thr Gly Cys Thr Ala Cys Thr Thr Cys Thr Thr Ala
                115                 120                 125
Thr Thr Cys Thr Gly Ala Thr Gly Gly Thr Thr Cys Cys Thr Thr Cys
            130                 135                 140
Thr Cys Ala Thr Gly Thr Ala Cys Thr Thr Thr Cys Cys Ala Ala Ala
145                 150                 155                 160
Ala Thr Gly Cys Thr Gly Gly Gly Gly Ala Thr Thr Ala Cys Thr Thr
                165                 170                 175
Ala Thr Gly Thr Cys Gly Thr Ala Gly Thr Gly Gly Thr Cys Thr Thr
                180                 185                 190
Thr Cys Thr Thr Thr Cys Gly Ala Thr Ala Gly Thr Ala Cys Thr Ala
                195                 200                 205
Ala Gly Ala Cys Cys Cys Ala Thr Cys Thr Cys Ala Ala Ala Thr
                210                 215                 220
Thr Gly Gly Thr Cys Gly Thr Ala Thr Ala Ala Gly Gly Cys Thr
225                 230                 235                 240
Gly Ala Thr Thr Thr Cys Ala Ala Ala Cys Thr Thr Gly Thr Cys Ala
                245                 250                 255
Ala Ala Cys Ala Ala Ala Thr Ala Gly Thr Thr Cys Cys Ala Ala
                260                 265                 270
Thr Gly Thr Thr Gly Gly Thr Thr Ala Thr Cys Cys Thr Ala Thr
                275                 280                 285
Gly Thr Thr Gly Gly Thr Gly Thr Thr Thr Ala Cys Gly Gly Thr Thr
            290                 295                 300
Gly Gly Ala Cys Thr Ala Gly Ala Ala Gly Thr Cys Cys Ala Cys Thr
305                 310                 315                 320
```

```
Thr Gly Thr Cys Gly Ala Ala Thr Ala Cys Thr Ala Cys Ala Thr Thr
                325                 330                 335
Gly Thr Cys Gly Ala Thr Ala Ala Thr Thr Gly Gly Cys Thr Thr Ala
            340                 345                 350
Gly Thr Cys Cys Ala Thr Cys Cys Ala Cys Cys Ala Gly Gly
            355                 360                 365
Thr Gly Ala Thr Thr Gly Gly Gly Thr Thr Gly Gly Thr Ala Ala Cys
    370                 375                 380
Ala Ala Gly Ala Ala Gly Thr Thr Thr Gly Gly Thr Thr Cys Thr Thr
385                 390                 395                 400
Thr Cys Ala Cys Thr Ala Thr Thr Gly Ala Thr Gly Gly Thr Gly Cys
            405                 410                 415
Thr Cys Ala Ala Thr Ala Cys Ala Cys Thr Gly Thr Thr Thr Ala Thr
            420                 425                 430
Gly Ala Ala Ala Ala Cys Ala Cys Thr Cys Gly Thr Ala Cys Thr Gly
        435                 440                 445
Gly Thr Cys Cys Ala Thr Cys Thr Ala Thr Thr Gly Ala Thr Gly Gly
    450                 455                 460
Thr Gly Ala Thr Ala Cys Cys Ala Cys Cys Thr Thr Cys Ala Ala Thr
465                 470                 475                 480
Cys Ala Ala Thr Ala Cys Thr Thr Thr Ala Gly Thr Ala Thr Thr Cys
            485                 490                 495
Gly Thr Cys Ala Ala Cys Ala Ala Gly Cys Thr Cys Gly Thr Gly Ala
            500                 505                 510
Thr Thr Gly Thr Gly Gly Thr Ala Cys Cys Ala Thr Thr Gly Ala Thr
        515                 520                 525
Ala Thr Thr Thr Cys Thr Gly Cys Thr Cys Ala Cys Thr Thr Thr Gly
530                 535                 540
Ala Thr Cys Ala Ala Thr Gly Gly Gly Ala Ala Ala Ala Gly Cys Thr
545                 550                 555                 560
Thr Gly Gly Thr Ala Thr Gly Ala Cys Thr Ala Thr Gly Gly Gly Thr
            565                 570                 575
Ala Ala Ala Thr Thr Ala Cys Ala Thr Gly Ala Ala Gly Cys Cys Ala
            580                 585                 590
Ala Gly Gly Thr Thr Thr Thr Ala Gly Gly Thr Gly Ala Ala Gly Cys
        595                 600                 605
Cys Gly Gly Thr Ala Ala Cys Gly Thr Thr Ala Ala Cys Gly Gly Thr
    610                 615                 620
Gly Gly Thr Gly Cys Cys Ala Gly Thr Gly Gly Thr Ala Cys Cys Gly
625                 630                 635                 640
Cys Thr Gly Ala Thr Thr Thr Cys Cys Cys Ala Thr Ala Cys Gly Cys
            645                 650                 655
Ala Ala Ala Gly Gly Thr Thr Thr Ala Cys Ala Thr Thr Gly Gly Thr
            660                 665                 670
Gly Ala Thr Thr Ala Gly
            675
```